United States Patent
Eom et al.

(10) Patent No.: US 12,023,171 B2
(45) Date of Patent: Jul. 2, 2024

(54) ANTIOXIDANT SENSOR AND METHOD OF OBTAINING ANTIOXIDANT SIGNAL

(71) Applicant: SAMSUNG ELECTRONICS CO., LTD., Suwon-si (KR)

(72) Inventors: Kun Sun Eom, Yongin-si (KR); Byung Hoon Ko, Hwaseong-si (KR); Jin Young Park, Hwaseong-si (KR); Sung Mo Ahn, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 1142 days.

(21) Appl. No.: 16/723,121

(22) Filed: Dec. 20, 2019

(65) Prior Publication Data

US 2020/0196935 A1   Jun. 25, 2020

(30) Foreign Application Priority Data

Dec. 20, 2018   (KR) .................. 10-2018-0166194

(51) Int. Cl.
*A61B 5/00*  (2006.01)
*A61B 5/1172*  (2016.01)

(52) U.S. Cl.
CPC .......... *A61B 5/443* (2013.01); *A61B 5/0075* (2013.01); *A61B 5/0077* (2013.01); *A61B 5/1172* (2013.01); *A61B 5/6897* (2013.01)

(58) Field of Classification Search
CPC ..... A61B 5/443; A61B 5/0075; A61B 5/0077; A61B 5/1172; A61B 5/6897
See application file for complete search history.

(56) References Cited

U.S. PATENT DOCUMENTS

| | | | |
|---|---|---|---|
| 6,292,576 B1 * | 9/2001 | Brownlee | G06V 40/12 340/5.83 |
| 7,133,710 B2 | 11/2006 | Acosta et al. | |
| 7,167,735 B2 * | 1/2007 | Uchida | G01N 21/552 600/316 |

(Continued)

FOREIGN PATENT DOCUMENTS

| | | |
|---|---|---|
| CN | 1698279 A | 11/2005 |
| CN | 104063678 A | 9/2014 |

(Continued)

OTHER PUBLICATIONS

Communication dated Feb. 13, 2020 issued by the European Intellectual Property Office in counterpart European Application No. 19218721.9.

(Continued)

*Primary Examiner* — Ashley K Buran
*Assistant Examiner* — Helene Bor
(74) *Attorney, Agent, or Firm* — Sughrue Mion, PLLC

(57) ABSTRACT

An antioxidant sensor according to an aspect of the disclosure includes: a touch sensor; a light source configured to emit light of a predetermined wavelength onto an object touching the touch sensor; a light receiver configured to receive light returning from the object; and a processor configured to extract an image of a contact surface of the object based on a sensor value of the touch sensor, to analyze the extracted image of the contact surface, and to obtain an antioxidant signal of the object by driving the light source based on a result of analyzing the image of the contact surface.

25 Claims, 24 Drawing Sheets

(56) References Cited

U.S. PATENT DOCUMENTS

| | | | |
|---|---|---|---|
| 7,251,518 B2 | 7/2007 | Herrmann | |
| 7,299,080 B2 | 11/2007 | Acosta et al. | |
| 8,260,402 B2 | 9/2012 | Ermakov et al. | |
| 8,335,550 B2 | 12/2012 | Segman | |
| 9,305,202 B2 | 4/2016 | Lin | |
| 9,489,096 B2 | 11/2016 | Johansson et al. | |
| 9,880,653 B2 | 1/2018 | Baharav et al. | |
| 10,362,996 B2* | 7/2019 | Kim | G01N 21/35 |
| 10,416,079 B2* | 9/2019 | Magnussen | G01N 21/474 |
| 10,948,346 B2 | 3/2021 | Kim | |
| 11,495,043 B2 | 11/2022 | Zhou et al. | |
| 2003/0044051 A1* | 3/2003 | Fujieda | G06V 40/40 |
| | | | 382/124 |
| 2005/0171413 A1 | 8/2005 | Blair | |
| 2005/0249386 A1 | 11/2005 | Juh | |
| 2006/0045315 A1* | 3/2006 | Saitoh | G06V 40/1335 |
| | | | 382/115 |
| 2009/0306521 A1* | 12/2009 | Ermakov | A61B 5/0075 |
| | | | 600/587 |
| 2010/0066697 A1* | 3/2010 | Jacomet | G06V 40/1394 |
| | | | 345/173 |
| 2012/0330164 A1 | 12/2012 | Ermakov et al. | |
| 2013/0100439 A1* | 4/2013 | Yu | G01N 21/255 |
| | | | 356/73 |
| 2013/0285977 A1 | 10/2013 | Baharav et al. | |
| 2014/0058224 A1 | 2/2014 | Gellermann et al. | |
| 2014/0200419 A1 | 7/2014 | Ermakov et al. | |
| 2015/0062078 A1* | 3/2015 | Christman | A61B 5/6897 |
| | | | 345/174 |
| 2015/0119725 A1 | 4/2015 | Martin et al. | |
| 2015/0148623 A1 | 5/2015 | Benaron | |
| 2015/0335293 A1* | 11/2015 | Christman | A61B 5/6826 |
| | | | 600/324 |
| 2015/0342527 A1 | 12/2015 | Karnik et al. | |
| 2016/0179245 A1 | 6/2016 | Johansson et al. | |
| 2016/0334332 A1 | 11/2016 | Magnussen et al. | |
| 2017/0079591 A1 | 3/2017 | Gruhlke et al. | |
| 2017/0095186 A1 | 4/2017 | Wu | |
| 2018/0177413 A1 | 6/2018 | Kwon et al. | |
| 2019/0021606 A1 | 1/2019 | Martin et al. | |

FOREIGN PATENT DOCUMENTS

| | | |
|---|---|---|
| CN | 108061714 A | 5/2018 |
| CN | 108846392 A | 11/2018 |
| EP | 3 238 017 B1 | 12/2018 |
| KR | 10-2008-0073988 A | 8/2008 |
| KR | 10-2011-0038020 A | 4/2011 |
| KR | 10-2011-0095027 A | 8/2011 |
| KR | 10-2015-0007322 A | 1/2015 |
| KR | 10-2015-0081251 A | 7/2015 |
| KR | 10-2016-0075584 A | 6/2016 |
| KR | 10-2016-0097174 A | 8/2016 |
| KR | 10-1672688 B1 | 11/2016 |
| KR | 10-2017-0010864 A | 2/2017 |
| KR | 10-1726613 B1 | 4/2017 |
| KR | 10-2017-0065176 A | 6/2017 |
| KR | 10-2018-0053746 A | 5/2018 |
| WO | 2016/105593 A1 | 6/2016 |

OTHER PUBLICATIONS

Communication issued on Dec. 15, 2023 by the Korean Intellectual Property Office in Korean Patent Application No. 10-2018-0166194.

Communication issued Mar. 19, 2024 by the State Intellectual Property Office of People's Republic of China in Chinese Patent Application No. 201911335470.2.

* cited by examiner

ANTIOXIDANT SENSOR AND METHOD OF OBTAINING ANTIOXIDANT SIGNAL

CROSS-REFERENCE TO RELATED APPLICATION(S)

This application claims priority from Korean Patent Application No. 10-2018-0166194, filed on Dec. 20, 2018, in the Korean Intellectual Property Office, the entire disclosure of which is incorporated herein by reference for all purposes.

BACKGROUND

1. Field

Example embodiments of the disclosure relate to an apparatus and a method for non-invasively obtaining an antioxidant signal and an apparatus and a method for measuring an antioxidant level.

2. Description of the Related Art

Reactive oxygen species are an important part of the biological defense mechanisms, such as white blood cells that protect the body against infections. However, it has been known that excessive production of reactive oxygen species in the body may lead to various diseases in tissues.

Common factors that cause the reactive oxygen species include stress, alcohol, peroxides, medicine, and the like. The reactive oxygen species produced by these factors may cause cranial nerve diseases, circulatory diseases, cancer, digestive tract diseases, liver diseases, arteriosclerosis, renal diseases, diabetes, aging, and the like.

Human bodies have a series of antioxidant defense systems to protect against oxygen toxicity. In order for such systems to normally operate, sufficient amounts of antioxidants are needed such as vitamin E, vitamin C, carotenoid, flavonoid, and the like. Thus, there is a need for an apparatus and a method for easily identifying the amount of antioxidants in the body.

SUMMARY

One or more example embodiments provide an antioxidant sensor and a method of measuring an antioxidant signal.

According to an aspect of an example embodiment, there is provided an antioxidant sensor, including: a touch sensor configured to detect a contact with an object; a first light source configured to emit light of a first wavelength onto the object; a light receiver configured to receive light returning from the object; and a processor configured to extract an image of a contact surface of the object based on a sensor value of the touch sensor, configured to analyze the extracted image of the contact surface, and configured to obtain an antioxidant signal of the object by driving the first light source based on a result of analyzing the image of the contact surface.

The antioxidant signal may include a signal associated with carotenoid.

The first wavelength may include a blue wavelength.

The processor may be further configured to determine a contact pressure reflection index by analyzing the extracted image of the contact surface, and based on the contact pressure reflection index being lower than or equal to a predetermined threshold, the processor may be further configured to obtain the antioxidant signal of the object by driving the first light source.

The contact pressure reflection index may include at least one of a change in an area of the contact surface, a change in a length of the contact surface, or a number of wrinkles in the image of the contact surface.

Based on the determined contact pressure reflection index being in a state of being lower than or equal to a predetermined threshold and the state being maintained for a predetermined period of time, the processor may be further configured to obtain the antioxidant signal of the object by driving the first light source.

Based on the determined contact pressure reflection index exceeding the predetermined threshold, the processor may be further configured to generate information for guiding a contact pressure between the object and the touch sensor to be increased, and output the information.

The light receiver may include at least one of a photodetector or a spectrometer.

The antioxidant sensor may include a second light source configured to emit light of a second wavelength onto the object touching the touch sensor, wherein the processor may be further configured to, based on the determined contact pressure reflection index being lower than or equal to a predetermined threshold, obtain a preprocessing signal of the object by driving the second light source and preprocess the obtained antioxidant signal based on the obtained preprocessing signal.

The second wavelength may include at least one of a blue wavelength, a green wavelength, or a red wavelength.

The processor may be further configured to normalize the antioxidant signal by subtracting the preprocessing signal from the antioxidant signal or by dividing the antioxidant signal by the preprocessing signal.

The processor may be further configured to determine an antioxidant level of the object by analyzing the obtained antioxidant signal.

The processor may be further configured to determine the antioxidant level of the object by using an antioxidant level estimation model which defines a relationship between the antioxidant signal and the antioxidant level.

The processor may be further configured to, based on the determined antioxidant level being lower than or equal to a predetermined threshold level, generate information recommending an increase of the antioxidant level and output the information.

According to an aspect of an example embodiment, there is provided a method of obtaining an antioxidant signal, including: detecting a contact with an object using a touch sensor; extracting an image of a contact surface of the object based on a sensor value of the touch sensor; and analyzing the extracted image of the contact surface, and obtaining an antioxidant signal of the object by emitting light of a first wavelength onto the object based on a result of the analyzing.

The antioxidant signal may include a signal associated with carotenoid.

The first wavelength may include a blue wavelength.

The obtaining the antioxidant signal may include: determining a contact pressure reflection index by analyzing the extracted image of the contact surface; and based on the contact pressure reflection index being lower than or equal to a predetermined threshold, obtaining the antioxidant signal of the object.

The contact pressure reflection index may include at least one of a change in an area of the contact surface, a change in a length of the contact surface, or a number of wrinkles in the image of the contact surface.

The obtaining the antioxidant signal may include, based on the determined contact pressure reflection index being in a state of being lower than or equal to a predetermined threshold and the state being maintained for a predetermined period of time, obtaining the antioxidant signal of the object.

Based on the determined contact pressure reflection index exceeding the predetermined threshold, generating information for guiding a contact pressure between the object and the touch sensor to be increased, and outputting the information.

The obtaining the antioxidant signal may include: obtaining a preprocessing signal of the object by emitting light of a second wavelength onto the object; and preprocessing the obtained antioxidant signal based on the obtained preprocessing signal.

The second wavelength may include at least one of a blue wavelength, a green wavelength, or a red wavelength.

The preprocessing of the obtained antioxidant signal may include normalizing the antioxidant signal by subtracting the preprocessing signal from the antioxidant signal or by dividing the antioxidant signal by the preprocessing signal.

The method may include determining an antioxidant level of the object by analyzing the obtained antioxidant signal.

The determining the antioxidant level may include determining the antioxidant level of the object by using an antioxidant level estimation model which defines a relationship between the antioxidant signal and the antioxidant level.

The method may include, based on the determined antioxidant level being lower than or equal to a predetermined threshold level, generating information recommending an increase of the antioxidant level and outputting the information.

According to an aspect of an example embodiment, there is provided an antioxidant sensor including: a light source configured to emit light onto an object; an optical fingerprint sensor configured to generate an image of a contact surface of the object that touches the optical fingerprint sensor based on light returning from the object; and a processor configured to obtain a skin spectrum of the object based on the light returning from the object, configured to analyze the image of the contact surface, and configured to determine an antioxidant level of the object by analyzing the skin spectrum based on a result of analyzing the image of the contact surface.

The light source may be further configured to emit visible light, including a blue wavelength, onto the object.

The light source may be provided in a display panel.

The optical fingerprint sensor may be provided in a complementary metal oxide semiconductor image sensor.

The processor may be further configured to determine a contact pressure reflection index by analyzing the image of the contact surface, and based on contact pressure reflection index being lower than or equal to a predetermined threshold, the processor may be further configured to determine the antioxidant level of the object by analyzing the skin spectrum.

The contact pressure reflection index may include at least one of a change in an area of the contact surface, a change in a length of the contact surface, or a number of wrinkles in the image of the contact surface.

Based on the determined contact pressure reflection index being in a state of being lower than or equal to a predetermined threshold and the state being maintained for a predetermined period of time, the processor may be further configured to determine the antioxidant level of the object by analyzing the skin spectrum.

Based on the determined contact pressure reflection index exceeding the predetermined threshold, the processor may be further configured to generate information for guiding a contact pressure between the object and the optical fingerprint sensor to be increased, and output the information.

The processor may be further configured to extract an absorbance of a first wavelength from the skin spectrum, and determines the antioxidant level of the object based on the extracted absorbance of the first wavelength.

The processor may be further configured to extract an absorbance of a second wavelength from the skin spectrum, and normalizes the absorbance of the first wavelength based on the extracted absorbance of the second wavelength.

The first wavelength may include a blue wavelength; and the second wavelength may include a blue wavelength, a green wavelength, or a red wavelength.

The processor may be further configured to normalize the absorbance of the first wavelength by subtracting the absorbance of the second wavelength from the absorbance of the first wavelength or by dividing the absorbance of the first wavelength by the absorbance of the second wavelength.

Based on the antioxidant level being lower than or equal to a predetermined threshold level, the processor may be further configured to generate information recommending an increase of the antioxidant level and output the information.

According to an aspect of an example embodiment, there is provided an antioxidant sensor, including: a touch sensor configured to detect a touch with an object; a spectrum measurer configured to measure a skin spectrum from the object; and a processor configured to: extract an image of a contact surface of the object based on a sensor value of the touch sensor, configured to determine a contact pressure reflection index by analyzing the extracted image of the contact surface, and based on the contact pressure reflection index being lower than or equal to a predetermined threshold, configured to obtain the skin spectrum by driving the spectrum measurer, and configured to determine an antioxidant level of the object by analyzing the obtained skin spectrum.

The spectrum measurer may include: a plurality of light sources configured to emit light of different wavelengths onto the object; a photodetector configured to receive light returning from the object; and a spectrum reconstructor configured to reconstruct the skin spectrum based on the received light.

The spectrum measurer may include: a light source configured to emit light of a predetermined wavelength onto the object; and a spectrometer configured to generate the skin spectrum by separating the light returning from the object.

Based on the determined contact pressure reflection index exceeding the predetermined threshold, the processor may be further configured to generate information for guiding a contact pressure between the object and the touch sensor to be increased, and output the information.

According to an aspect of an example embodiment, there is provided an antioxidant sensor, including: a fingerprint sensor configured to detect a contact with an object, and configured to generate an image of a contact surface of the object; a light source configured to emit light of a predetermined wavelength onto the object; a light receiver configured to receive light returning from the object; and a processor configured to analyze the generated image of the contact surface, and configured to obtain an antioxidant signal of the object by driving the light source based on a result of analyzing the image of the contact surface.

The processor may be further configured to determine a contact pressure reflection index by analyzing the generated image of the contact surface, and based on the determined contact pressure reflection index being in a state of being lower than or equal to a predetermined threshold and the state being maintained for a predetermined period of time, the processor may be further configured to obtain the antioxidant signal of the object by driving the light source.

The contact pressure reflection index may include at least one of a change in an area of the contact surface, a change in a length of the contact surface, or a number of wrinkles in the image of the contact surface.

Based on the determined contact pressure reflection index exceeding the predetermined threshold, the processor may be further configured to generate information for guiding a contact pressure between the object and the fingerprint sensor to be increased, and output the information.

The processor may be further configured to detect a fingerprint by analyzing the generated image of the contact surface, and identify a user based on the detected fingerprint.

BRIEF DESCRIPTION OF THE DRAWINGS

The above and/or other aspects of the disclosure will become apparent and more readily appreciated from the following description of the example embodiments, taken in conjunction with the accompanying drawings, in which.

DETAILED DESCRIPTION

Figure 1:
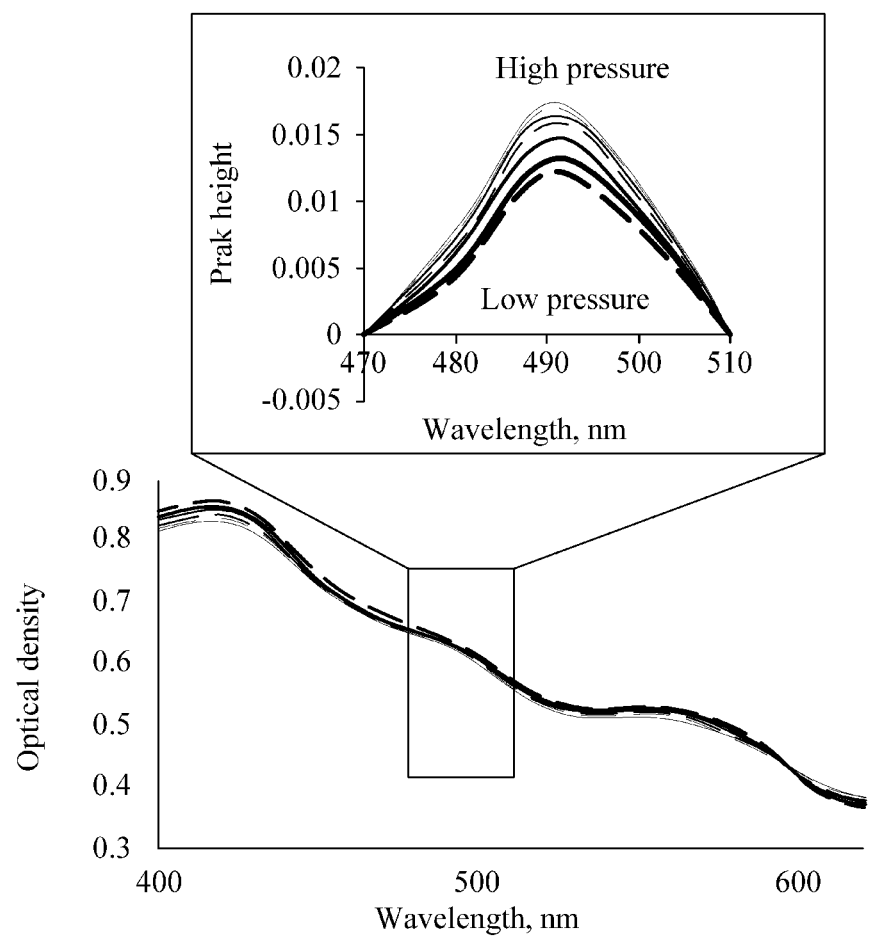
FIG. 1 is an example diagram illustrating a change in an optical density spectrum of skin according to a contact pressure applied to the skin.

Hereinafter, example embodiments of the disclosure will be described in detail with reference to the accompanying drawings. It should be noted that, in the drawings, the same reference symbols refer to same parts although illustrated in other drawings. In the following description, a detailed description of known functions and configurations incorporated herein will be omitted when it may obscure the subject matter of the disclosure.

Throughout the drawings and the detailed description, unless otherwise described, the same drawing reference numerals will be understood to refer to the same elements, features, and structures. The relative size and depiction of these elements may be exaggerated for clarity, illustration, and convenience.

Process steps described herein may be performed differently from a specified order, unless a specified order is clearly stated as being necessary in the context of the disclosure. That is, each step may be performed in a specified order, at substantially the same time, in a reverse order, or in any other order different from the specified order.

Further, the terms used throughout this specification are defined in consideration of the functions according to example embodiments, and can be varied according to a purpose and an application of the functions and the like. Therefore, definitions of the terms should be understood based on the overall context.

It will be understood that, although the terms first, second, etc. may be used herein to describe various elements, these elements should not be limited by these terms. These terms are only used to distinguish one element from another. Any references to a singular element may include plural elements unless expressly stated otherwise. In the specification, it should be understood that the terms, such as 'including' or 'having,' etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Further, components that will be described in the specification are discriminated merely according to functions mainly performed by the components. That is, two or more components which will be described later can be integrated into a single component. Furthermore, a single component which will be explained later can be separated into two or more components. Moreover, each component which will be described can additionally perform some or all of a function executed by another component in addition to the main function thereof. Some or all of the main function of each component Which will be explained can be carried out by another component. Each component may be implemented as hardware, software, or a combination of both.

Figure 2:
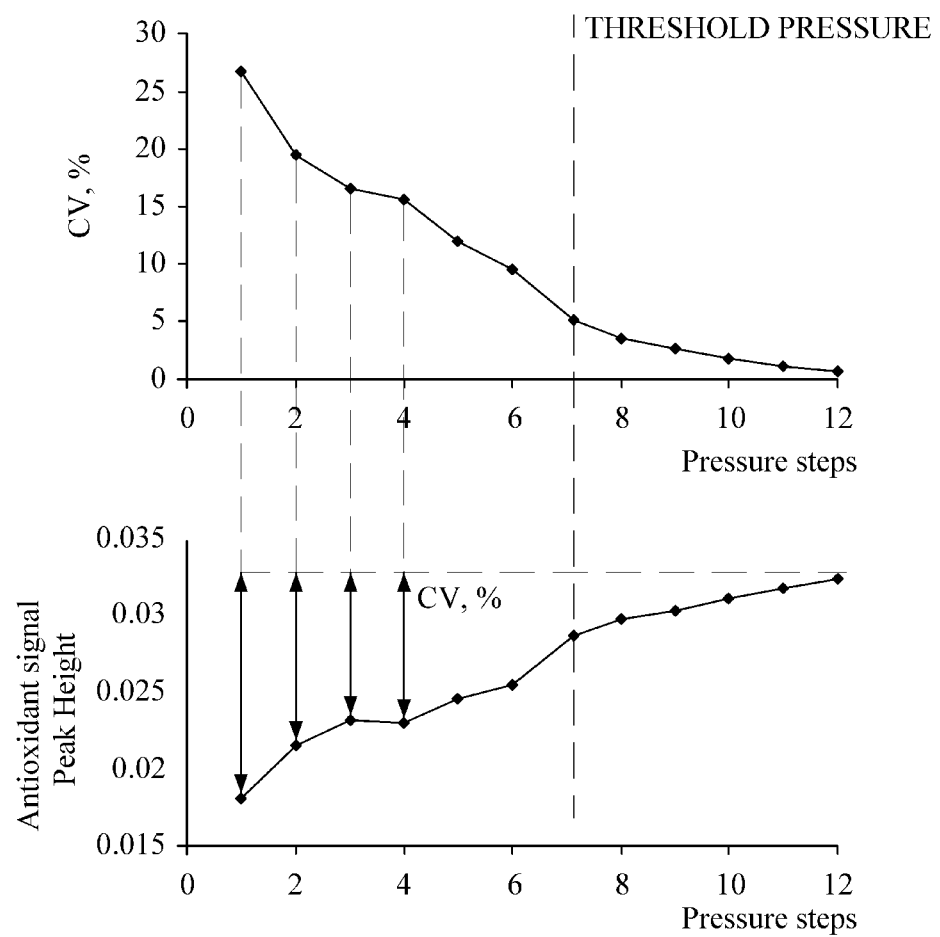
FIG. 2 is an example diagram illustrating a change in an antioxidant signal in skin according to a contact pressure applied to the skin.

FIG. 1 is an example diagram illustrating a change in an optical density spectrum of skin according to a contact pressure applied to the skin, and FIG. 2 is an example diagram illustrating a change in an antioxidant signal in skin according to a contact pressure applied to the skin. In FIGS. 1-2, the term "pressure steps" refers to a magnitude of a pressure applied to the skin, and the higher the pressure step is, the higher the magnitude of a pressure applied to the skin is.

Referring to FIG. 1, an optical density spectrum of skin is changed according to a pressure applied to the skin. For example, it can be seen from the example of FIG. 1 that in a wavelength band of about 470 nm to about 510 nm, a peak height increases as a contact pressure applied to skin increases. Here, the wavelength band of about 470 nm to about 510 nm may be included in a wavelength band in which an antioxidant signal is obtained, e.g., an absorption band of an antioxidant substance (e.g., carotenoid). Further, the peak height may indicate optical density, from which interference caused by a substance other than an antioxidant substance is eliminated by a preprocessing process (e.g., baseline correction, normalization, etc.).

Referring to FIG. 2, it can be seen that as a contact pressure applied to skin increases, a peak height of an antioxidant signal increases, and at a pressure greater than or equal to a predetermined level applied to the skin, an antioxidant signal is saturated, e.g., converges to a predetermined value and stabilized. Further, it can be seen that a coefficient of variation (CV) of the peak height of an antioxidant signal decreases as a contact pressure applied to skin increases.

Figure 3:
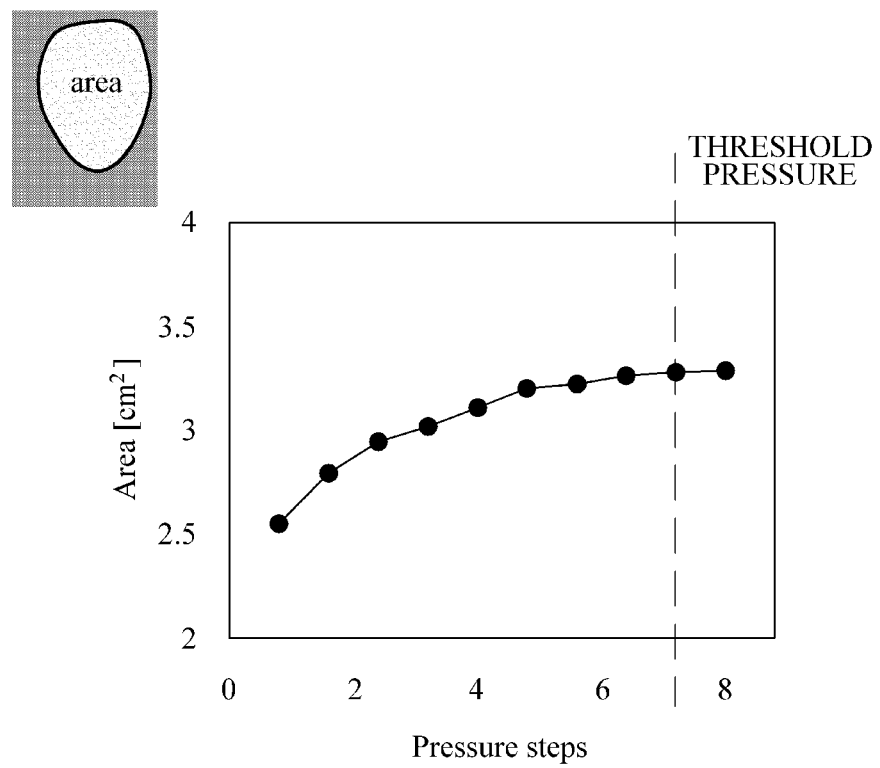
FIG. 3 is an example diagram illustrating a relationship between a contact pressure applied to skin and a contact area.
Figure 4:
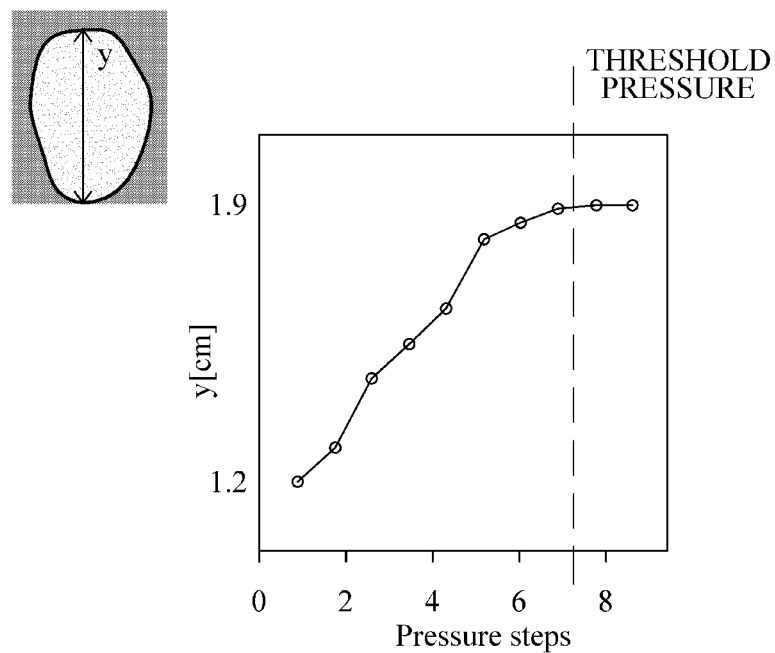
FIGS. 4 and 5 are example diagrams illustrating a relationship between a contact pressure applied to skin and a length of a contact surface.
Figure 5:
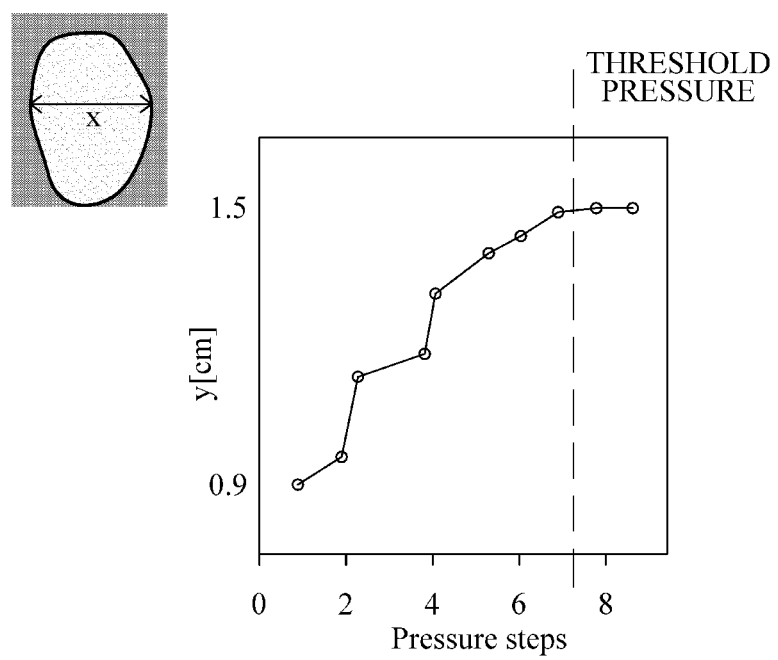
Figure 6:
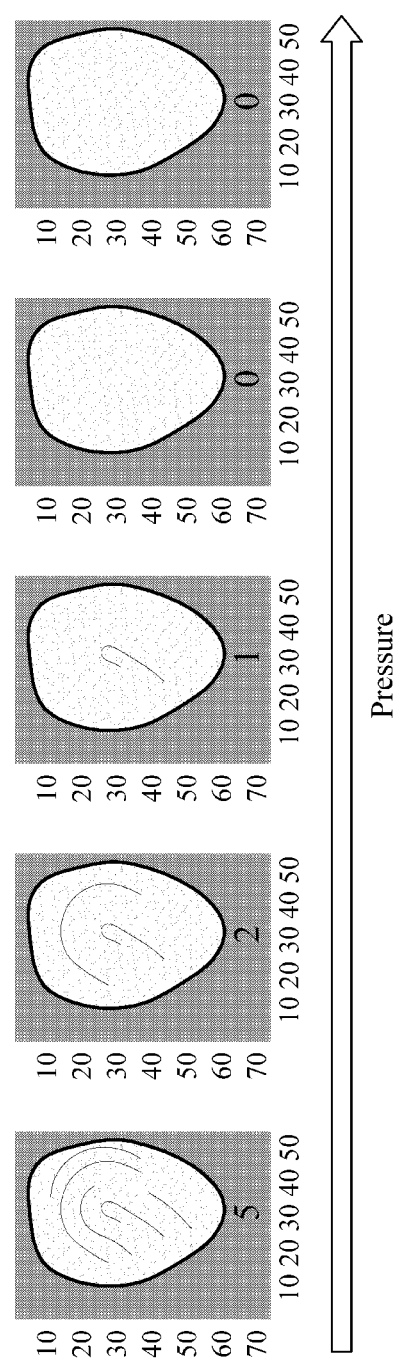
FIG. 6 is an example diagram illustrating a relationship between a contact pressure applied to skin and a number of wrinkles extracted from an image of a contact surface.

FIG. 3 is an example diagram illustrating a relationship between a contact pressure applied to skin and a contact area; FIGS. 4 and 5 are example diagrams illustrating a relationship between a contact pressure applied to skin and a length of a contact surface; and FIG. 6 is an example diagram illustrating a relationship between a contact pressure applied to skin and a number of wrinkles extracted from an image of a contact surface. In FIGS. 3-6, the term "pressure steps" refers to a magnitude of a pressure applied to the skin, and the higher the pressure step is, the higher the magnitude of a pressure applied to the skin is.

Referring to FIGS. 3 to 6, a contact area, a length of a contact surface, and a number of wrinkles extracted from an image of the contact surface may vary according to a contact pressure applied to skin. In the example of FIG. 3, as a contact pressure applied to skin increases, a contact area increases; and at a pressure greater than or equal to a predetermined level applied to the skin, the contact area may converge to a predetermined value. In the examples of FIGS. 4 and 5, as a contact pressure applied to skin increases, a length (y) in a long axis (or longitudinal axis) direction and a length (x) in a short axis (or a width axis) direction of a contact surface increase; and at a pressure greater than or equal to a predetermined level applied to the skin, the length (y) in the long axis direction and the length (x) in the short axis of the contact surface may converge to a predetermined value. In the example of FIG. 6, as a contact pressure applied to skin increases, the number of wrinkles extracted from the image of the contact surface is reduced; and at a pressure greater than or equal to a predetermined level applied to the skin, the number of wrinkles extracted from the image of the contact surface may become zero.

Accordingly, a pressure applied to skin may be estimated by analyzing at least one of the contact area, the length (e.g., the long-axis direction length (y) and the short-axis direction length (x)) of the contact surface, and the number of wrinkles extracted from the image of the contact surface; and an antioxidant signal may be obtained by guiding a user to apply a pressure, which is greater than or equal to a threshold pressure, to the object based on the estimated pressure, such that an antioxidant signal having a high signal-to-noise ratio may be obtained without using a pressure sensor.

Figure 7:
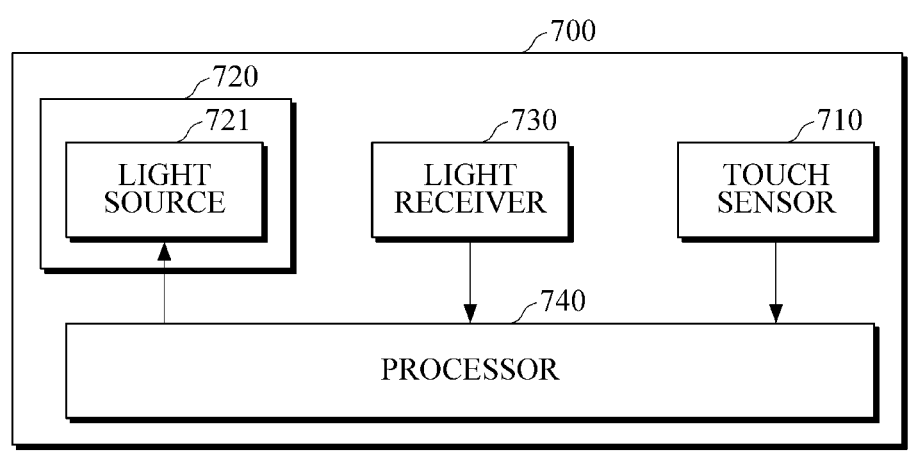
FIG. 7 is a diagram illustrating an antioxidant sensor according to an example embodiment.

FIG. 7 is a diagram illustrating an example of an antioxidant sensor 700 according to an example embodiment. The antioxidant sensor 700 of FIG. 7 is an apparatus for non-invasively measuring an antioxidant level of an object, and may be embedded in an electronic device, or may be enclosed in a housing to be provided as a separate device. Examples of the electronic device may include a cellular phone, a smartphone, a tablet PC, a laptop computer, a personal digital assistant (PDA), a portable multimedia player (PMP), a navigation, an MP3 player, a digital camera, a wearable device, and the like; and examples of the wearable device may include a wristwatch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. However, the electronic device is not limited to the above examples, and the wearable device is neither limited thereto.

Referring to FIG. 7, the antioxidant sensor 700 includes a touch sensor 710, a light source part 720, a light receiver 730, and a processor 740. Here, the processor 740 may include one or more processors, a memory, and/or a combination thereof.

The touch sensor 710 may detect a contact with an object. The touch sensor 710 may be of one or more various types such as a capacitive type, a resistive type, an infrared type, an acoustic wave type, a pressure type, and the like.

The light source part 720 includes a light source 721 which emits light of a predetermined wavelength onto an object according to a predetermined control signal. The light source 721 may emit light of, for example, a blue wavelength, which is included in a wavelength band, e.g., an absorption band of an antioxidant substance (e.g., carotenoid), onto the object. In an example embodiment, the light source 721 may include a light emitting diode (LED), an organic light emitting diode (OLED), a Quantum dot light-emitting diode (QLED), a laser diode, a fluorescent body, and the like.

In addition, the light source part 720 may further include at least one optical element (e.g., mirror, etc.) for directing the light emitted by the light source 721 toward a desired position of the object.

The light receiver 730 may receive light reflected or scattered from the object. In an example embodiment, the light receiver 730 may be provided in a photodetector or a spectrometer. Here, the photodetector may receive light reflected or scattered from an object, and may convert the received light into an electric signal, and may include a photo diode, a photo transistor (PTr), a charge-coupled device image sensor (CCD image sensor), a complementary metal oxide semiconductor image sensor (CIS), and the like. Further, the spectrometer may receive light reflected or scattered from an object and may separate the received light.

The spectrometer may include an interference spectrometer, a grating spectrometer, a prism spectrometer, and the like.

Further, the light receiver 730 may further include at least one optical element (e.g., mirror, etc.) for directing light reflected or scattered from an object toward the light receiver 730.

The processor 740 may control the overall operation of the antioxidant sensor 700.

Once an object touches the touch sensor 710, the processor 740 may extract an image of a contact surface of the object based on a sensor value of the touch sensor 710. For example, the processor 740 may extract the image of the contact surface by performing contouring based on the sensor value of the touch sensor 710.

The processor 740 may analyze the extracted image of the contact surface, and may obtain an antioxidant signal by controlling the light source 721 based on the analysis of the extracted image of the contact surface. In this case, the antioxidant signal may be a signal associated with carotenoid accumulated in the epidermis. For example, the processor 740 may determine a contact pressure reflection index; and if the contact pressure reflection index is lower than or equal to a predetermined threshold, the processor 740 may drive the light source 721 to obtain an antioxidant signal of the object. Alternatively, if the contact pressure reflection index is lower than or equal to a predetermined threshold value, and such a state is maintained for a predetermined period of time, the processor 740 may drive the light source 721 to obtain an antioxidant signal of the object. Here, the contact pressure reflection index may include at least one of a change in the area of the contact surface, a change in the length of the contact surface, and the number of wrinkles in the extracted image of the contact surface.

In an example embodiment, the processor 740 may determine a change in the area of the contact surface by analyzing the image of the contact surface. The change in the area of the contact surface may be calculated by subtracting a preceding value from a current value or by dividing the current value by the preceding value. However, this is merely an example and the disclosure is not limited thereto. Further, if the change in the area of the contact surface is less than or equal to a first threshold, or if the change in the area of the contact surface is less than or equal to the first threshold and such a state is maintained for a predetermined period of time, the processor 740 may determine that a pressure applied to the object is sufficient to obtain an antioxidant signal. Based on this determination, the processor 740 may drive the light source 721 to emit light of a predetermined wavelength onto the object, and ay obtain an antioxidant signal by controlling the light receiver 730 to receive light returning from the object. According to an example embodiment, the processor 740 may start to drive the light source 721 and/or the light receiver 730 upon determining that the change in the area of the contact surface satisfies a preset condition (e.g., if the change in the area of the contact surface is less than or equal to the first threshold or if such a state is maintained for a predetermined period of time).

In another example embodiment, the processor 740 may determine a change in the length of the contact surface by analyzing the image of the contact surface. The length of the contact surface may include a length in any direction such as a length in a long axis direction, a length in a short axis direction, a length in a diagonal direction, and the like; and the change in the length may be calculated by subtracting a preceding value from a current value or by dividing the current value by the preceding value. However, this is merely example and the disclosure is not limited thereto. If the change in the length of the contact surface is less than or equal to a second threshold, or if the change in the length of the contact surface is less than or equal to the second threshold and such a state is maintained for a predetermined period of time, the processor 740 may determine that a pressure applied to the object is sufficient to obtain an antioxidant signal. Based on this determination, the processor 740 may drive the light source 721 to emit light of a predetermined wavelength onto the object, and ay obtain an antioxidant signal by controlling the light receiver 730 to receive light returning from the object. According to an example embodiment, the processor 740 may start to drive the light source 721 and/or the light receiver 730 upon determining that the change in the length of the contact surface satisfies a preset condition (e.g., if the change in the length of the contact surface is less than or equal to the second threshold or if such a state is maintained for a predetermined period of time).

In yet another example embodiment, the processor 740 may determine the number of wrinkles in the image of the contact surface by analyzing the image of the contact surface. If the number of wrinkles is less than or equal to a third threshold, or if the number of wrinkles is less than or equal to the third threshold and such a state is maintained for a predetermined period of time, the processor 740 may determine that a pressure applied to the object is sufficient to obtain an antioxidant signal. Based on this determination, the processor 740 may drive the light source 721 to emit light of a predetermined wavelength onto the object, and may obtain an antioxidant signal by controlling the light receiver 730 to receive light returning from the object. According to an example embodiment, the processor 740 may start to drive the light source 721 and/or the light receiver 730 upon determining that the change in the number of wrinkles in the image of the contact surface satisfies a preset condition (e.g., if the change in the number of wrinkles is less than or equal to the third threshold or if such a state is maintained for a predetermined period of time).

The first threshold, the second threshold, and the third threshold may be preset in consideration of pressure at which the antioxidant signal is saturated and stabilized.

If the contact pressure reflection index exceeds a predetermined threshold, or even if the contact pressure reflection index is lower than or equal to a predetermined threshold, if the state is not maintained for a predetermined period of time, the processor 740 may determine that a pressure applied to the object is not sufficient to obtain an antioxidant signal, and may generate information on a low contact pressure and/or guidance information for guiding a user to increase the pressure applied to the object and output the generated information through an output device. The output device may include all types of devices such as, for example, a visual output device (e.g., display, etc.), an audio output device (e.g., speaker, etc.), and a tactile output device (e.g., vibrator, etc.).

Upon obtaining the antioxidant signal, the processor 740 may determine an antioxidant level of the object by analyzing the obtained antioxidant signal. For example, the processor 740 may determine the antioxidant level of the object by using an antioxidant level estimation model. Here, the antioxidant level estimation model defines a relationship between an antioxidant signal and an antioxidant level, and may be pre-generated by, for example, regression analysis or machine learning and stored in an internal or an external database of the processor 740. The antioxidant level estimation model may be built in the form of a mathematical algorithm or a matching table, but is not limited thereto.

In response to an antioxidant level being lower than or equal to a predetermined threshold level, the processor 740 may generate information on the antioxidant level and/or information recommending a user to increase the antioxidant level and may provide the generated information to a user through the output device described above. For example, in response to an antioxidant level being lower than or equal to a predetermined threshold level, the processor 740 may generate recommendation information, such as "eat more vegetables," "cut down on smoking," "cut down on alcohol consumption," "exercise more," "reduce stress," and the like, and may provide the recommendation information to the user through the output device.

Figure 8:
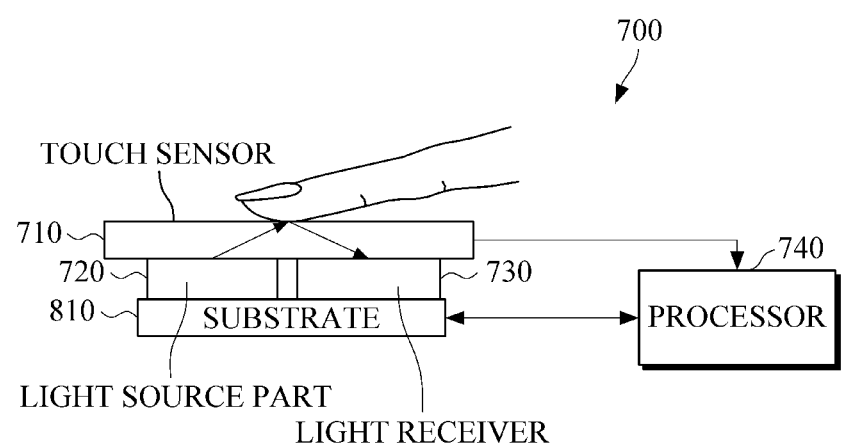
FIG. 8 is a diagram illustrating a structure of an antioxidant sensor according to an example embodiment.

FIG. 8 is a diagram illustrating an example of a structure of an antioxidant sensor according to an example embodiment.

Referring to FIG. 8, the touch sensor 710 may be disposed on an outer surface of the antioxidant sensor 700 to come into contact with an object. The light source part 720 and the light receiver 730 are provided on a substrate 810 and are disposed below the touch sensor 710, to emit light onto the object and to receive light returning from the object, respectively. The processor 740 may be associated with the substrate 810 and the touch sensor 710, to transmit and receive data to and from the touch sensor 710, the light source part 720, and the light receiver 730.

In addition, the touch sensor 710 may comprise a transparent material so as not to block light emitted by the light source part 720 onto the object and light returning from the object.

Figure 9:
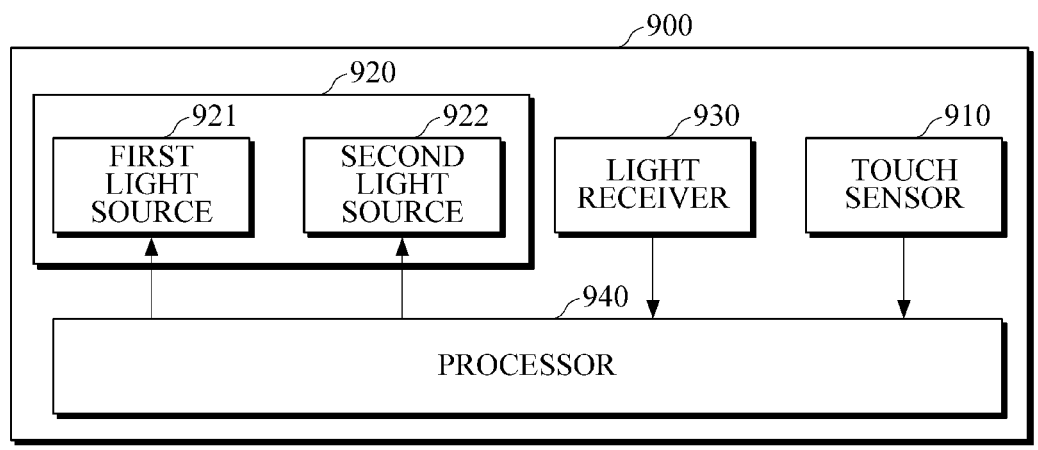
FIG. 9 is a diagram illustrating an antioxidant sensor according to another example embodiment.

FIG. 9 is a diagram illustrating an example of an antioxidant sensor 900 according to another example embodiment. The antioxidant sensor 900 of FIG. 9 is a device which may non-invasively obtain an antioxidant level of an object, and may be embedded in the electronic device described above or may be enclosed in a housing to be provided as a separate device.

Referring to FIG. 9, the antioxidant sensor 900 includes a touch sensor 910, a light source part 920, a light receiver 930, and a processor 940. Here, the processor 940 may include one or more processors, a memo and a combination thereof. The touch sensor 910, the light receiver 930, and the processor 940 of FIG. 9 have functions similar to those of the light touch sensor 710, the light receiver 730, and the processor 740, such that overlapping descriptions will be omitted.

The light source part 920 includes a first light source 921 which emits light of a first wavelength, and a second light source 922 which emits light of a second wavelength.

The first light source 921 may be a light source used for obtaining an antioxidant signal. The first light source may include a blue wavelength which is included in an absorption band of an antioxidant substance (e.g., carotenoid).

The second light source 922 may be a light source used for obtaining a signal which is used for preprocessing an antioxidant signal obtained by driving the first light source 921 (hereinafter referred to as a preprocessing signal). The second wavelength may be a wavelength different from the first wavelength, and may include at least one of a blue wavelength, a green wavelength, and a red wavelength.

Once the object touches the touch sensor 910, the processor 940 may extract an image of a contact surface of the object based on a sensor value of the touch sensor 910, may determine a contact pressure reflection index by analyzing the extracted image of the contact surface. Based on the contact pressure reflection index, the processor 940 may control the first light source 921 and the second light source 922 to obtain the antioxidant signal and the preprocessing signal. Further, the processor 940 may preprocess the antioxidant signal based on the preprocessing signal. For example, the processor 940 may normalize the antioxidant signal by subtracting the preprocessing signal from the antioxidant signal or by dividing the antioxidant signal by the preprocessing signal. By normalizing the antioxidant signal, the processor 940 may eliminate an effect of a substance, other than an antioxidant substance, from the obtained antioxidant signal. In addition, the processor 940 may determine an antioxidant level of the object by analyzing the preprocessed antioxidant signal. For example, the processor 940 may determine the antioxidant level of the object by using an antioxidant level estimation model.

While FIG. 9 illustrates an example where the light source part 920 includes two light sources 921 and 922, this is merely an example for convenience of explanation, and the light source part 920 is not limited thereto. That is, the light source part 920 may include a plurality of light sources (e.g., three or more light sources) which may obtain the preprocessing signal, in which case each of the plurality of light sources may emit light of the same wavelength, or may emit light of different wavelengths such as a blue wavelength, a green wavelength, or a red wavelength. In this case, the processor 940 may drive each of the plurality of light sources to obtain a plurality of preprocessing signals, and may preprocess the antioxidant signal by using the plurality of preprocessing signals. For example, the processor 940 may preprocess the antioxidant signal by performing baseline correction based on the plurality of preprocessing signals.

Figure 10:
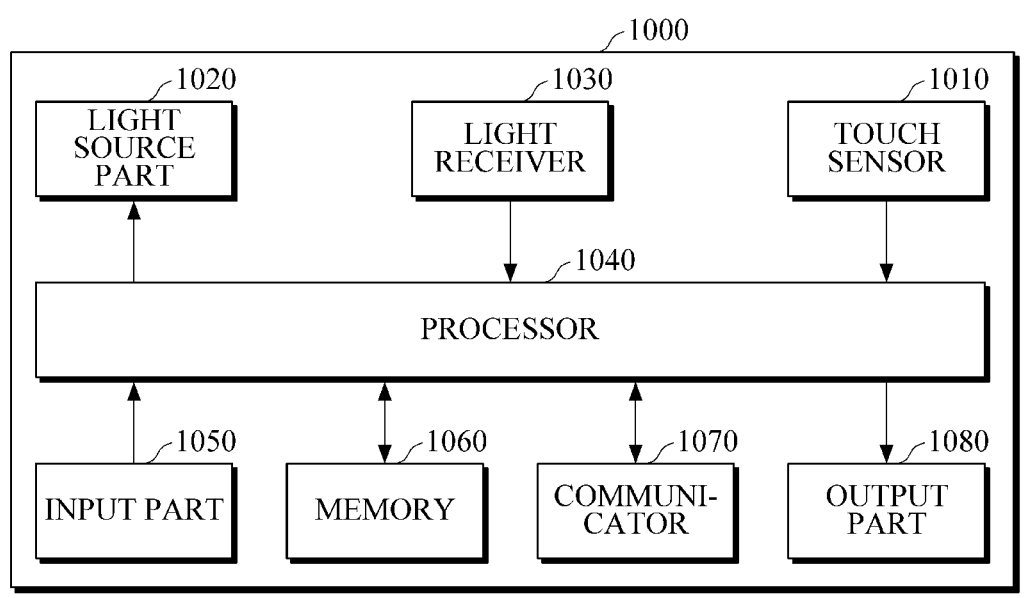
FIG. 10 is a diagram illustrating an antioxidant sensor according to another example embodiment.

FIG. 10 is a diagram illustrating an example of an antioxidant sensor 1000 according to another example embodiment. The antioxidant sensor 1000 of FIG. 10 is a device which may non-invasively measure an antioxidant level of an object, and may be embedded in the electronic device described above or may be enclosed in a housing to be provided as a separate device.

Referring to FIG. 10, the antioxidant sensor 1000 includes a touch sensor 1010, a light source part 1020, a light receiver 1030, a processor 1040, an input part 1050, a memory 1060, a communicator 1070, and an output part 1080. Here, the touch sensor 1010, the light source part 1020, the light receiver 1030, and the processor 1040 are the same as or similar to the touch sensors 710 and 910, the light source parts 720 and 920, the light receivers 730 and 930, and the processors 740 and 940 described above with reference to FIGS. 7 and 9, such that detailed description thereof will be omitted.

The input part 1050 may receive an input of one or more of various operation signals from a user. In an example embodiment, the input part 1050 may include, for example but not limited to, a keypad, a dome switch, a touch pad (static pressure/capacity cc), a jog wheel, a jog switch, a hardware (H/W) button, and the like. Particularly, the touch pad, which forms a layer structure with a display, may be called a touch screen.

The memory 1060 may store programs or commands for operation of the antioxidant sensor 1000, and may store data input to and output from the antioxidant sensor 1000. Further, the memory 1060 may store data processed by the antioxidant sensor 1000, data (e.g., antioxidant level estimation model) usable for data processing of the antioxidant sensor 1000, and the like.

The memory 1060 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like. Further, the antioxidant sensor 1000 may operate an external storage medium, such as web storage and the like, which performs a storage function of the memory 1060 on the Internet.

The communicator 1070 may perform communication with an external device. For example, the communicator 1070 may transmit, to the external device, data used by the antioxidant sensor 1000, processing result data of the antioxidant sensor 1000, and the like; or may receive, from the external device, various data usable for obtaining an antioxidant signal and/or determining an antioxidant level.

The external device may be medical equipment that uses the data used by the antioxidant sensor 1000 or the processing result data of the antioxidant sensor 1000, a printer to print out results, and/or a display to display the results. In addition, the external device may be a digital TV, a desktop computer, a cellular phone, a smartphone, a tablet PC, a laptop computer, a personal digital assistant (PDA), a portable multimedia player (PMP), a navigation, an MP3 player, a digital camera, a wearable device, and the like. However, these are merely examples and the external device is not limited thereto.

The communicator 1070 may communicate with an external device by using Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, this is merely example and is not intended to be limiting.

The output part 1080 may output the data used by the antioxidant sensor 1000, the processing result data of the antioxidant sensor 1000, and the like. In an example embodiment, the output part 1080 may output the data used by the antioxidant sensor 1000, the processing result data of the antioxidant sensor 1000, and the like by using, for example but not limited to, at least one of an acoustic method, a visual method, and a tactile method. To this end, the output part 1080 may include a display, a speaker, a vibrator, and the like.

Figure 11:
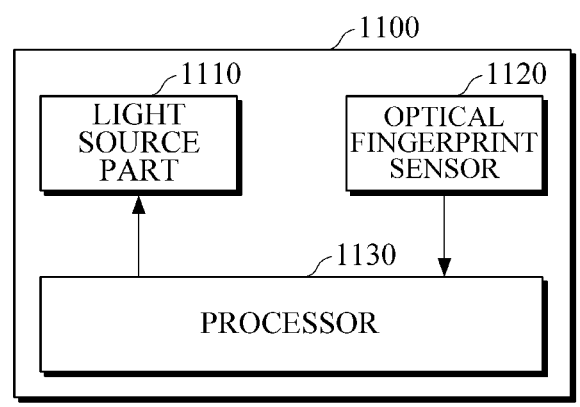
FIG. 11 is a diagram illustrating an antioxidant sensor according to another example embodiment.

FIG. 11 is a diagram illustrating an example of an antioxidant sensor 1100 according to another example embodiment. The antioxidant sensor 1100 of FIG. 11 is an apparatus for non-invasively obtaining an antioxidant level of an object, and may be embedded in the electronic device described above or may be enclosed in a housing to be provided as a separate device.

Referring to FIG. 11, the antioxidant sensor 1100 includes a light source part 1110, an optical fingerprint sensor 1120, and a processor 1130.

The light source part 1110 includes at least one light source which emits light of a predetermined wavelength onto an object. The light source part 1110 may emit visible light, including a blue wavelength which is included in an absorption band of an antioxidant substance (e.g., carotenoid), onto the object. In an example embodiment, the light source part 1110 may be implemented as a display panel, to use a light-emitting element of the display panel as a light source.

The optical fingerprint sensor 1120 may receive light reflected or scattered from the object. In an example embodiment, the optical fingerprint sensor 1120 may be implemented as a complementary metal oxide semiconductor image sensor (CIS).

The optical fingerprint sensor 1120 may include a plurality of pixels, which may be divided into at least two pixel groups including a first pixel group for generating an image of a contact surface of the object and a second pixel group for obtaining a skin spectrum of the object. A color filter may be mounted at least some pixels of the second pixel group to receive light in a wavelength band, in which an antioxidant signal may be obtained.

The optical fingerprint sensor 1120 may generate an image of a contact surface based on light received by the first pixel group.

The processor 1130 may control the overall operation of the antioxidant sensor 1100.

The processor 130 may obtain a skin spectrum of the object based on light received by the second pixel group of the optical fingerprint sensor 1120. In this case, the skin spectrum may be a skin absorption spectrum.

The processor 1130 may determine an antioxidant level based on the generated image of the contact surface and the obtained skin spectrum. For example, the processor 1130 may determine a contact pressure reflection index by analyzing the image of the contact surface. Further, if the contact pressure reflection index is lower than or equal to a predetermined threshold, or if the pressure reflection index is lower than or equal to a predetermined threshold and such a state is maintained for a predetermined period of time, the processor 1130 may extract an absorbance of a predetermined wavelength, corresponding to an antioxidant signal, from the skin spectrum, and may determine an antioxidant level of the object by analyzing the absorbance of the predetermined wavelength. The predetermined wavelength may be included in a wavelength band in which an antioxidant signal is obtained, e.g., a blue wavelength included in an absorption band of an antioxidant substance (e.g., carotenoid). The processor 1130 may determine the antioxidant level of the object by using, for example, the antioxidant level estimation model described above. In addition, the contact pressure reflection index may include at least one of a change in the area of the contact surface, a change in the length of the contact surface, and a change in the number of wrinkles in the image of the contact surface.

In an example embodiment, the processor 1130 may determine a change in the area of the contact surface by analyzing the image of the contact surface. In this case, the change in the area may be calculated by subtracting a preceding value from a current value or by dividing the current value by the preceding value. However, this is merely an example and the disclosure is not limited thereto. Further, if the change in the area of the contact surface is less than or equal to a first threshold, or if the change in the area of the contact surface is less than or equal to the first threshold and such a state is maintained for a predetermined period of time, the processor 1130 may determine that the skin spectrum is measured under sufficient pressure, and may determine the antioxidant level of the object by analyzing the skin spectrum.

In another example embodiment, the processor 130 may determine a change in the length of the contact surface by analyzing the image of the contact surface. In this case, the length of the contact surface may include a length in any direction such as a length in a long axis direction, a length in a short axis direction, a length in a diagonal direction, and the like; and the change in the length may be calculated by, for example, subtracting a preceding value from a current value or by dividing the current value by the preceding value. If the change in the length of the contact surface is less than or equal to a second threshold, or if the change in the length of the contact surface is less than or equal to the second threshold and such a state is maintained for a predetermined period of time, the processor 1130 may determine that the skin spectrum is measured under sufficient pressure, and may determine the antioxidant level of the object by analyzing the skin spectrum.

In yet another example embodiment, the processor 1130 may determine the number of wrinkles in the image of the contact surface by analyzing the image of the contact surface. If the number of wrinkles is less than or equal to a third threshold, or if the number of wrinkles is less than or equal to the third threshold and such a state is maintained for a predetermined period of time, the processor 1130 may determine that the skin spectrum is measured under sufficient pressure, and may determine the antioxidant level of the object by analyzing the skin spectrum.

Before determining the antioxidant level of the object, the processor 1130 may preprocess the absorbance of the predetermined wavelength corresponding to the antioxidant signal. In an example embodiment, the processor 1130 may extract an absorbance which is used for preprocessing (hereinafter a preprocessing absorbance), corresponding to the preprocessing signal, from the skin spectrum, and may preprocess the absorbance of the predetermined wavelength based on the extracted preprocessing absorbance. For example, the processor 1130 may extract the preprocessing absorbance at one or more wavelengths, and may preprocess the absorbance of the predetermined wavelength by performing normalization or baseline correction of the absorbance of the predetermined wavelength based on the extracted preprocessing absorbance. In this manner, the processor 1130 may eliminate an effect of a substance, other than an antioxidant substance, from the absorbance of the predetermined wavelength corresponding to the antioxidant signal. The one or more wavelengths, at which the preprocessing absorbance is extracted, may be a wavelength different from the predetermined wavelength corresponding to the antioxidant signal, and may be a blue wavelength, a green wavelength, or a red wavelength.

If the contact pressure reflection index exceeds a predetermined threshold, or even if the contact pressure reflection index is lower than or equal to a predetermined threshold, if such a state is not maintained for a predetermined period of time, the processor 1130 may determine that the skin spectrum is not measured with a sufficient pressure. In an example embodiment, the processor 1130 may generate information on a low contact pressure and/or guidance information for guiding a user to increase a pressure applied to an object and output the generated information through the output device described above.

In response to an antioxidant level being lower than or equal to a predetermined threshold level, the processor 1130 may generate information, for example, information on the antioxidant level and/or recommendation information recommending a user to increase the antioxidant level and may provide the generated information to the user through the output device described above.

Figure 12:
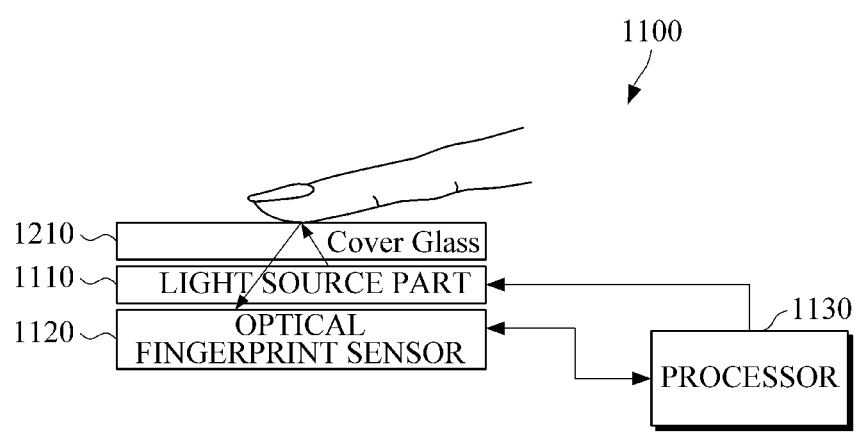
FIG. 12 is a diagram illustrating a structure of an antioxidant sensor according to another example embodiment.

FIG. 12 is a diagram illustrating an example of a structure of an antioxidant sensor according to another example embodiment.

Referring to FIG. 12, a cover glass 1210 may be disposed on an outer surface of the antioxidant sensor 1100 to come into contact with an object. The light source part 1110 (e.g., display panel) is disposed below the cover glass 1210, and may emit light onto the object touching the cover glass 1210. The optical fingerprint sensor 1120 (e.g., CIS sensor) is disposed below the light source part 1110 to receive light returning from the object. The processor 1130 may be connected to the light source part 1110 and the optical fingerprint sensor 1120 to transmit and receive data to and from the light source part 1110 and the optical fingerprint sensor 1120.

Figure 13:
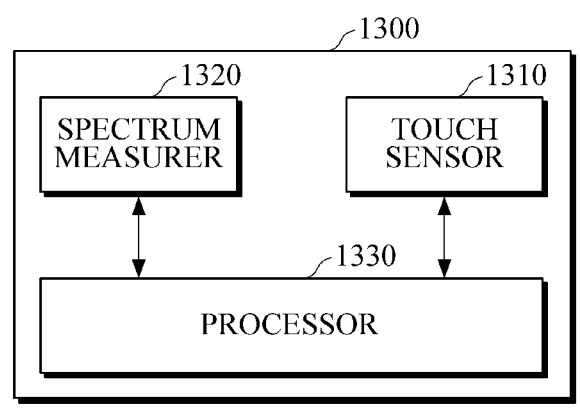
FIG. 13 is a diagram illustrating an antioxidant sensor according to another example embodiment.

FIG. 13 is a diagram illustrating an example of an antioxidant sensor 1300 according to another example embodiment. The antioxidant sensor 1300 of FIG. 13 is a device for non-invasively measuring an antioxidant level of an object, and may be embedded in the electronic device described above or may be enclosed in a housing to be provided as a separate device.

Referring to FIG. 13, the antioxidant sensor 1300 includes a touch sensor 1310, a spectrum measurer 1320, and a processor 1330. Here, the processor 1330 may include one or more processors, a memory, and/or a combination thereof.

The touch sensor 1310 may detect a contact with an object. The touch sensor 1310 may be of one or more of various types such as a capacitive type, a resistive type, an infrared type, an acoustic wave type, a pressure type, and the like.

The spectrum measurer 1320 may measure a skin spectrum according to a predetermined control signal. The skin spectrum may be a skin absorption spectrum. The spectrum measurer 1320 will be described in detail later with reference to FIGS. 14 and 15.

The processor 1330 may control the overall operation of the antioxidant sensor 1300.

Once an object touches the touch sensor 1310, the processor 1330 may extract an image of a contact surface of the object based on a sensor value of the touch sensor 1310. For example, the processor 1330 may extract the image of the contact surface by performing contouring based on the sensor value of the touch sensor 1310.

The processor 1330 may analyze the extracted image of the contact surface, and may obtain a skin spectrum of the object by controlling the spectrum measurer 1320 based on the analysis of the extracted image of the contact surface. For example, the processor 1330 may determine a contact pressure reflection index by analyzing the extracted image of the contact surface; and if the contact pressure reflection index is lower than or equal to a predetermined threshold, the processor 1330 may control the spectrum measurer 1320 to measure the skin spectrum of the object. Alternatively, if the contact pressure reflection index is lower than or equal to a predetermined threshold and such a state is maintained for a predetermined period of time, the processor 1330 may control the spectrum measurer 1320 to measure the skin spectrum of the object. Here, the contact pressure reflection index may include at least one of a change in the area of the contact surface, a change in the length of the contact surface, and the number of wrinkles in the image of the contact surface.

In an example embodiment, the processor 1330 may determine the change in the area of the contact surface by analyzing the image of the contact surface. The change in the area may be calculated by, for example, subtracting a preceding value from a current value or by dividing the current value by the preceding value. Further, if the change in the area of the contact surface is less than or equal to a first threshold, or if the change in the area of the contact surface is less than or equal to the first threshold and such a state is maintained for a predetermined period of time, the processor 1330 may control the spectrum measurer 1320 to measure the skin spectrum of the object.

In another example embodiment, the processor 1330 may determine the change in the length of the contact surface by analyzing the image of the contact surface. The length of the contact surface may include a length in any direction such as a length in a long axis direction, a length in a short axis direction, a length in a diagonal direction, and the like; and the change in the length may be calculated by, for example, subtracting a preceding value from a current value or by dividing the current value by the preceding value. In addition, if the change in the length of the contact surface is less than or equal to a second threshold, or if the change in the length of the contact surface is less than or equal to the second threshold and such a state is maintained for a predetermined period of time, the processor 1330 may control the spectrum measurer 1320 to measure the skin spectrum of the object.

In yet another example embodiment, the processor 1330 may determine the number of wrinkles in the image of the contact surface by analyzing the image of the contact surface. If the number of wrinkles is less than or equal to a third threshold value, or if the number of wrinkles is less than or equal to the third threshold value and such a state is maintained for a predetermined period of time, the processor 1330 may control the spectrum measurer 1320 to measure the skin spectrum of the object.

The first threshold, the second threshold, and the third threshold may be preset in consideration of pressure at which the antioxidant signal is saturated and stabilized.

If the contact pressure reflection index exceeds a predetermined threshold, or even if the contact pressure reflection index is lower than equal to a predetermined threshold, if such a state is not maintained for a predetermined period of time, the processor 1330 may generate information on a low contact pressure and/or guidance information for guiding a user to increase a pressure applied to an object and output the generated information through an output device described above.

Upon measuring the skin spectrum, the processor 1330 may determine an antioxidant level of the object by analyzing the measured skin spectrum. For example, the processor 1330 may extract an absorbance of a predetermined wavelength, corresponding to an antioxidant signal, from the skin spectrum, and may determine the antioxidant level of the object by analyzing the absorbance of the predetermined wavelength corresponding to the antioxidant signal. In this case, the predetermined wavelength corresponding to the antioxidant signal may be included in a wavelength band in which an antioxidant signal is obtained, e.g., a blue wavelength included in an absorption band of an antioxidant substance (e.g., carotenoid). The processor 1330 may determine the antioxidant level of the object by using the antioxidant level estimation model described above.

Before determining the antioxidant level of the object, the processor 1330 may preprocess the absorbance of the predetermined wavelength corresponding to the antioxidant signal. In an example embodiment, the processor 1330 may extract an absorbance which is used for preprocessing (hereinafter a preprocessing absorbance), corresponding to the preprocessing signal, from the skin spectrum, and may preprocess the absorbance of the predetermined wavelength, corresponding to the antioxidant signal, based on the extracted preprocessing absorbance. For example, the processor 1330 may extract the preprocessing absorbance at one or more wavelengths, and may preprocess the absorbance of the predetermined wavelength, corresponding to the antioxidant signal, by performing normalization or baseline correction of the absorbance of the predetermined wavelength, corresponding to the antioxidant signal, based on the extracted preprocessing absorbance. In this manner, the processor 1130 may eliminate an effect of a substance, other than an antioxidant substance, from the absorbance of the predetermined wavelength corresponding to the antioxidant signal. In this case, the one or more wavelengths, at which the preprocessing absorbance is extracted, may be a wavelength different from the predetermined wavelength corresponding to the antioxidant signal, and may be a blue wavelength, a green wavelength, or a red wavelength.

If the contact pressure reflection index exceeds a predetermined threshold, or even if the contact pressure reflection index is lower than equal to a predetermined threshold, if such a state is not maintained for a predetermined period of time, the processor 1330 may generate information on a low contact pressure and/or guidance information for guiding a user to increase a pressure applied to an object and output the generated information through the output device described above.

In response to an antioxidant level being lower than or equal to a predetermined threshold level, the processor 1330 may generate information on the antioxidant level and/or information recommending a user to increase the antioxidant level and may provide the generated information to a user through the output device described above.

Figure 14:
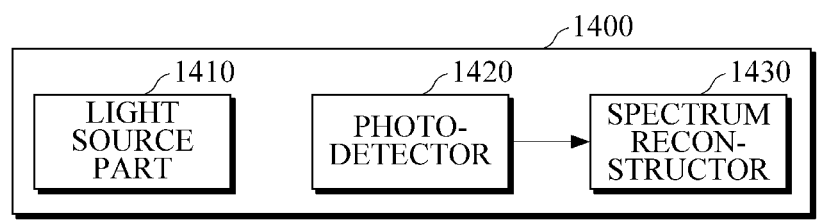
FIG. 14 is a diagram illustrating a spectrum measurer according to an example embodiment.

FIG. 14 is a diagram illustrating an example of a spectrum measurer 1400 according to an example embodiment. The spectrum measurer 1400 of FIG. 14 may be an example of the spectrum measurer 1320 of FIG. 13.

Referring to FIG. 14, the spectrum measurer 1400 includes a light source part 1410, a photodetector 1420, and a spectrum reconstructor 1430.

The light source part 1410 may include a plurality of light sources which emit light of different wavelengths onto an object. Each of the light sources may emit visible light, having a blue wavelength, a green wavelength, and a red wavelength, onto an object. In an example embodiment, each of the light sources may include alight emitting diode (LED), an organic light emitting diode (OLED), a Quantum dot light-emitting diode (QLED), a laser diode, a fluorescent body, and the like, and may include a white light source. The light source part 1410 may further include at least one optical element (e.g., mirror, etc.) for directing the light emitted by each of the light sources toward a desired position of an object.

The photodetector 1420 may receive light reflected or scattered from a user's skin, and may convert the received light into an electric signal. The photodetector 1420 may include a photo diode, a photo transistor (PTr), a charge-coupled device image sensor (CCD image sensor), a complementary metal oxide semiconductor image sensor (CIS), and the like. Further, the photodetector 1420 may not be necessarily a single device, and may be formed as an array of a plurality of devices.

There may be various numbers and arrangements of light sources and photodetectors, and the number and arrangement thereof may vary according to a purpose of use of the spectrum measurer 1400, the size and shape of the electronic device in which the spectrum measurer 1400 is embedded, and the like.

The spectrum reconstructor 1430 may obtain a skin spectrum of an object by reconstructing a spectrum using the received light and a light source spectrum. The light source spectrum may refer to a spectrum of light emitted by each light source, and information on the light source spectrum may be pre-stored in an internal or an external database.

In an example embodiment, the spectrum reconstructor 1430 may obtain a skin spectrum of an object using the following Equation 1.

$$R=[S_i \times S_{PD}]^{-1} \times M_{PD} \qquad \text{[Equation 1]}$$

Herein, R denotes the skin spectrum of the object, $S_i$ denotes the light source spectrum, $S_{PD}$ denotes sensitivity for each wavelength of the photodetector, and $M_{PD}$ denotes a measured value of the photodetector.

Figure 15:
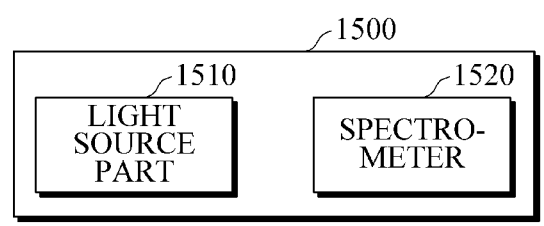
FIG. 15 is a diagram illustrating a spectrum measurer according to another example embodiment.

FIG. 15 is a diagram illustrating an example of a spectrum measurer 1500 according to another example embodiment. The spectrum measurer 1500 of FIG. 15 may be an example of the spectrum measurer 1320 of FIG. 13.

Referring to FIG. 15, the spectrum measurer 1500 includes a light source part 1510 and a spectrometer 1520.

The light source part 1510 may include one light source which emits white light onto an object or a plurality of light sources which emit light of different wavelengths onto the object. The light source part 1510 may further include at least one optical element (e.g., mirror, etc.) for directing the light emitted by each of the light sources toward a desired position of an object The spectrometer 1520 may receive light reflected or scattered from the object, and may generate a skin spectrum by separating the received light. The spectrometer 1520 may be of one or more various types, such as an interference spectrometer, a grating spectrometer, a prism spectrometer, and the like; and may include various optical elements, such as a diffraction grating, a prism, a hologram filter, a dielectric lens, or a combination thereof.

Figure 16:
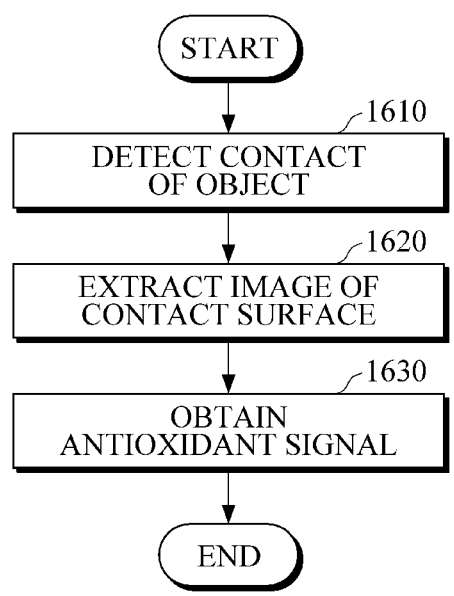
FIG. 16 is a diagram illustrating a method of obtaining an antioxidant signal according to an example embodiment.

FIG. 16 is a diagram illustrating an example of a method of obtaining an antioxidant signal according to an example embodiment. The antioxidant signal obtaining method of FIG. 16 may be performed by any one of the antioxidant sensors 700, 900, and 1000 of FIGS. 7, 9, and 10.

Referring to FIG. 16, the antioxidant sensor may detect a contact with an object using the touch sensor in 1610.

The antioxidant sensor may extract an image of a contact surface of the object based on a sensor value of the touch sensor in 1620. For example, the antioxidant sensor may extract the image of the contact surface by performing contouring based on the sensor value of the touch sensor.

The antioxidant sensor may analyze the extracted image of the contact surface and may obtain an antioxidant signal based on the analysis in 1630. The antioxidant signal may be a signal associated with carotenoid accumulated in the epidermis. For example, the antioxidant sensor may determine a contact pressure reflection index based on the mage of the contact surface, may compare the contact pressure reflection index with a predetermined threshold, and may obtain the antioxidant signal based on a result the comparison. For example, the antioxidant sensor ay selectively obtain the antioxidant signal based on a result of comparison between the contact pressure reflection index and the predetermined threshold. The contact pressure reflection index may include at least one of a change in the area of the contact surface, a change in the length of the contact surface, and the number of wrinkles in the image of the contact surface. The predetermined threshold may be preset in consideration of pressure at which the antioxidant signal is saturated and stabilized.

Figure 17:
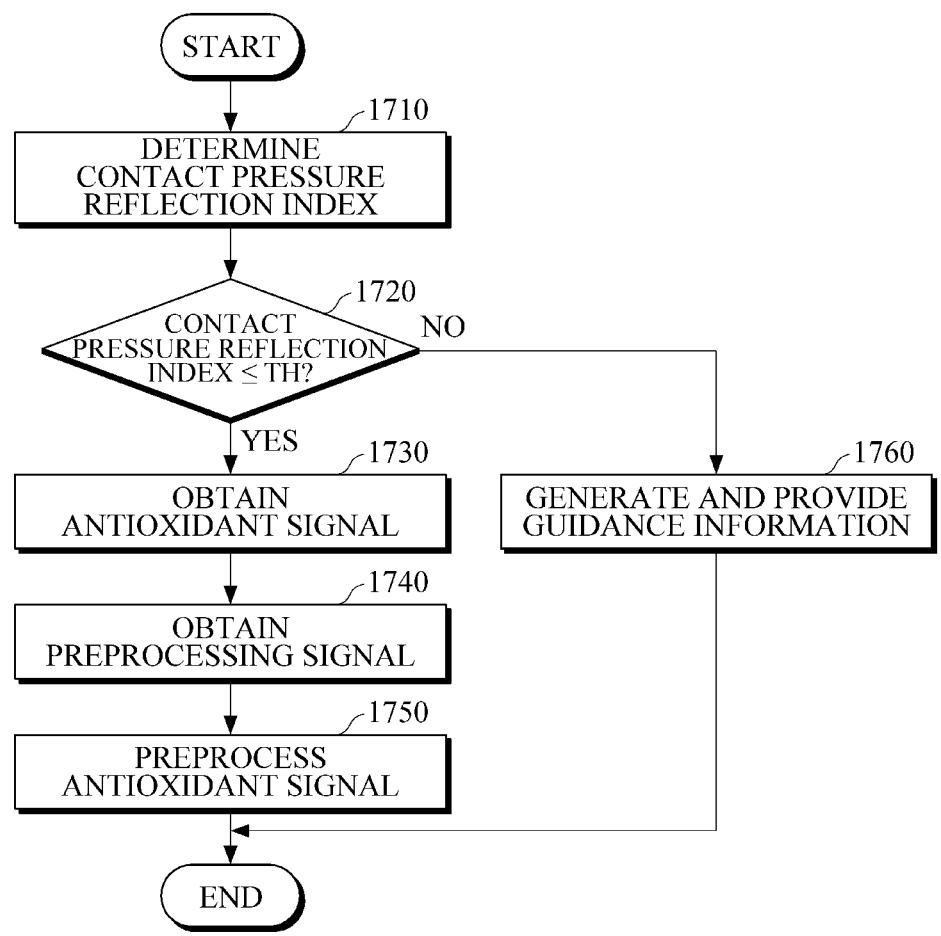
FIG. 17 is a diagram illustrating a method of obtaining an antioxidant signal based on analysis of an image of a contact surface according to an example embodiment.

FIG. 17 is a diagram illustrating an example of a method of obtaining an antioxidant signal based on analysis of an image of a contact surface according to an example embodiment. The antioxidant signal obtaining method of FIG. 17 may be an example of the obtaining of an antioxidant signal in 1630 of FIG. 16.

Referring to FIG. 17, the antioxidant sensor determines a contact pressure reflection index by analyzing the image of the contact surface in 1710, and may compare the contact pressure reflection index with a predetermined threshold in 1720. In response to the contact pressure reflection index being lower than or equal to the predetermined threshold, the antioxidant sensor may obtain the antioxidant signal by emitting light of a predetermined wavelength onto an object in 1730 (or by controlling to start emitting light of a predetermined wavelength onto the object). The predetermined wavelength may include a blue wavelength.

In an example embodiment, the antioxidant sensor may determine a change in the area of the contact surface by analyzing the image of the contact surface. Further, in response to the change in the area of the contact surface being less than a first threshold, the antioxidant sensor may emit light of a predetermined wavelength onto an object (or by control to start emitting light of a predetermined wavelength onto the object), and may obtain an antioxidant signal by receiving light returning from the object.

In another example embodiment, the antioxidant sensor may determine a change in the length of the contact surface by analyzing the image of the contact surface. Further, in response to the change in the length of the contact surface being less than a second threshold, the antioxidant sensor may emit light of a predetermined wavelength onto an object (or by control to start emitting light of a predetermined wavelength onto the object), and may obtain an antioxidant signal by receiving light returning from the object.

In yet another example embodiment, the antioxidant sensor may determine the number of wrinkles in the image of the contact surface by analyzing the image of the contact surface. Further, in response to the number of wrinkles being less than or equal to a third threshold, the antioxidant sensor may emit light of a predetermined wavelength onto an object (or by control to start emitting light of a predetermined wavelength onto the object), and may obtain an antioxidant signal by receiving light returning from the object.

In addition, the antioxidant sensor may further consider a duration of a status of the contact pressure reflection index in addition to a magnitude thereof. For example, in response to determining that the contact pressure reflection index has a status of being lower than or equal to a predetermined threshold and such a state being maintained for a predetermined period of time, the antioxidant sensor may obtain the antioxidant signal.

The antioxidant sensor may obtain a preprocessing signal by emitting light of another wavelength onto the object in 1740. For example, the antioxidant sensor may emit light of another wavelength onto the object, and may obtain the preprocessing signal by receiving light of another wavelength returning from the object. The another wavelength may be a wavelength different from the predetermined wavelength used for obtaining the antioxidant signal, and may include at least one of a blue wavelength, a green wavelength, and a red wavelength.

The antioxidant sensor may preprocess the antioxidant signal based on the preprocessing signal in 1750. For example, the antioxidant sensor may normalize the antioxidant signal by subtracting the preprocessing signal from the antioxidant signal or by dividing the antioxidant signal by the preprocessing signal. In this manner, the antioxidant sensor may eliminate an effect of a substance, other than an antioxidant substance, from the obtained antioxidant signal.

In response to the contact pressure reflection index exceeding a predetermined threshold, the antioxidant sensor may generate information on a low contact pressure and/or guidance information for guiding a user to increase a pressure applied to an object and may output the generated information through the output device described above in 1760.

Figure 18:
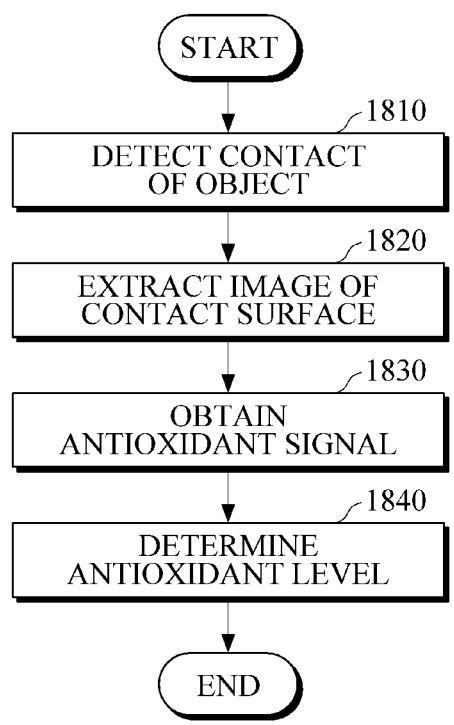
FIG. 18 is a diagram illustrating a method of obtaining an antioxidant signal according to another example embodiment.

FIG. 18 is a diagram illustrating an example of a method of obtaining an antioxidant signal according to another example embodiment. The antioxidant signal obtaining method of FIG. 18 may be performed by any one of the antioxidant sensors 700, 900, and 1000 of FIGS. 7, 9, and 10. Operations 1810, 1820, and 1830 of FIG. 18 are the same as or similar to the operations 1610, 1620 and 1630 of FIG. 16, such that detailed description thereof will be omitted.

Referring to FIG. 18, the antioxidant sensor may determine an antioxidant level of an object by analyzing an obtained antioxidant signal in 1840. For example, the antioxidant sensor may determine the antioxidant level of the object by using an antioxidant level estimation model. Here, the antioxidant level estimation model defines a relationship between an antioxidant signal and an antioxidant level, and may be pre-generated by, for example, regression analysis or machine learning.

In response to the antioxidant level being lower than or equal to a predetermined threshold level, the antioxidant sensor may generate information on the antioxidant level and/or information recommending a user to increase the antioxidant level. For example, the antioxidant sensor may generate recommendation information, such as "eat more vegetables," "cut down on smoking," "cut down on alcohol consumption," "exercise more," "reduce stress," and the like, and may provide the recommendation information to a user through an output device.

Figure 19:
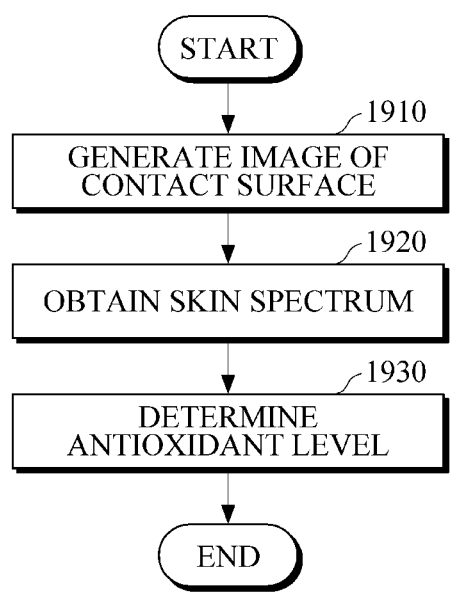
FIG. 19 is a diagram illustrating a method of obtaining an antioxidant signal according to another example embodiment.

FIG. 19 is a diagram illustrating an example of a method of obtaining an antioxidant signal according to another example embodiment. The antioxidant signal obtaining method of FIG. 19 may be performed by the antioxidant sensor 1100 of FIG. 11.

Referring to FIG. 19, the antioxidant sensor may emit light onto an object, and may generate an image of a contact surface of the object by receiving light returning from the object in 1910. Further, the antioxidant sensor may obtain a skin spectrum of the object based on the received light in 1920.

The antioxidant sensor may determine an antioxidant level based on the image of the contact surface and the skin spectrum in 1930.

Figure 20:
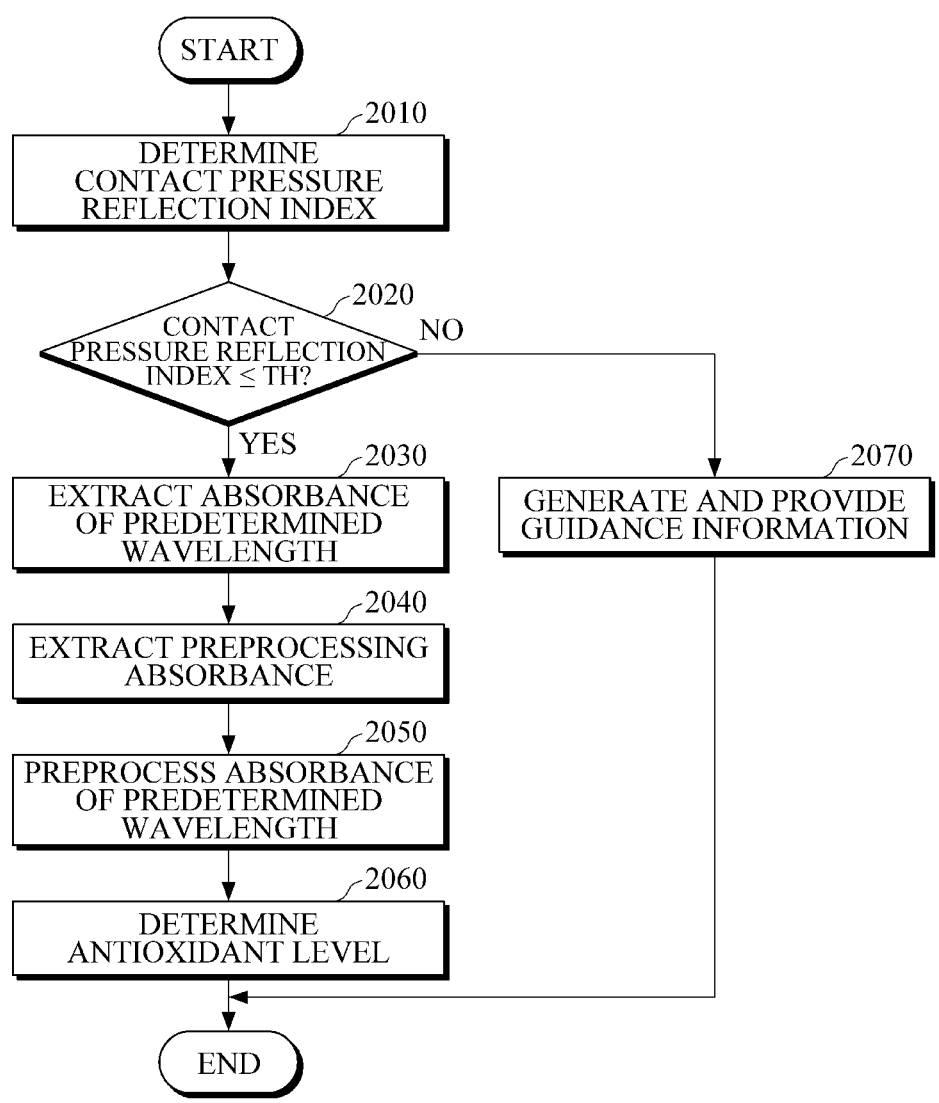
FIG. 20 is a diagram illustrating a method of determining an antioxidant level according to an example embodiment.

FIG. 20 is a diagram illustrating an example of determining an antioxidant level according to an example embodiment. The antioxidant level determining method of FIG. 20 may be an example of the determining of an antioxidant level 1930 of FIG. 19.

Referring to FIG. 20, the antioxidant sensor may determine a contact pressure reflection index by analyzing an image of a contact surface in 2010, and may compare the contact pressure reflection index with a predetermined threshold TI in 2020.

In response to the contact pressure reflection index being lower than or equal to the predetermined threshold, the antioxidant sensor may extract an absorbance of a predetermined wavelength, corresponding to an antioxidant signal, from a skin spectrum in 2030, and may extract an absorbance of another wavelength, which is used for preprocessing (hereinafter a preprocessing absorbance) corresponding to a preprocessing signal in 2040. The predetermined wavelength corresponding to the antioxidant signal may be a blue wavelength; and the another wavelength may be a wavelength different from the predetermined wavelength corresponding to the antioxidant signal, and may be a blue wavelength, a green wavelength, or a red wavelength.

In addition, the antioxidant sensor may further consider a duration of a status of the contact pressure reflection index in addition to a magnitude thereof. For example, in response to the contact pressure reflection index being lower than or equal to a predetermined threshold and such a state being maintained for a predetermined period of time, the antioxidant sensor may extract the absorbance of the predetermined wavelength corresponding to the antioxidant signal and the preprocessing absorbance.

The antioxidant sensor may preprocess the absorbance of the predetermined wavelength, corresponding to the antioxidant signal, based on the preprocessing absorbance in 2050. The antioxidant sensor may normalize the absorbance of the predetermined wavelength corresponding to the antioxidant signal by, for example, subtracting the preprocessing absorbance from the absorbance of the predetermined wavelength corresponding to the antioxidant signal or by dividing the absorbance of the predetermined wavelength corresponding to the antioxidant signal by the preprocessing absorbance. By normalizing the absorbance of the predetermined wavelength, the antioxidant sensor may eliminate an effect of a substance, other than an antioxidant substance, from the absorbance of the predetermined wavelength corresponding to the antioxidant signal.

The antioxidant sensor may determine an antioxidant level of the object by analyzing the preprocessed absorbance of the predetermined wavelength in 2060.

In response to the contact pressure reflection index exceeding a predetermined threshold, the antioxidant sensor may generate information on a low contact pressure and/or guidance information for guiding a user to increase a pressure applied to the object, and may output the generated information to the user through the output device described above in 2070.

In addition, in response to the antioxidant level being lower than or equal to a predetermined threshold level, the antioxidant sensor may generate information on the antioxidant level and/or information recommending a user to increase the antioxidant level, and may output the generated information to the user through the output device.

Figure 21:
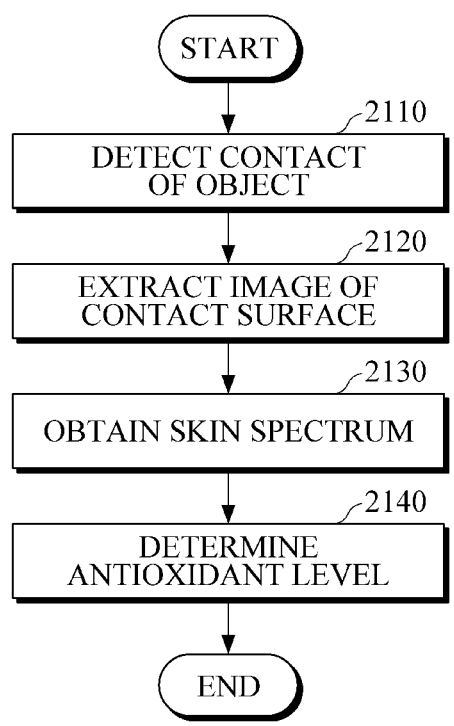
FIG. 21 is a diagram illustrating a method of obtaining an antioxidant signal according to another example embodiment.

FIG. 21 is a diagram illustrating an example of a method of obtaining an antioxidant signal according to another example embodiment. The antioxidant signal obtaining method of FIG. 21 may be performed by the antioxidant sensor 1300 of FIG. 13.

Referring to FIG. 21, the antioxidant sensor may detect a contact with an object through a touch sensor in 2110.

The antioxidant sensor may extract an image of a contact surface of the object based on a sensor value of the touch sensor in 2120. For example, the antioxidant sensor may extract the image of the contact surface by performing contouring based on the sensor value of the touch sensor.

The antioxidant sensor may analyze the extracted image of the contact surface and may obtain a skin spectrum of the object based on the analysis in 2130. For example, the antioxidant sensor may determine a contact pressure reflection index based on the image of the contact surface, may compare the contact pressure reflection index with a predetermined threshold, and may obtain the skin spectrum of the object based on the comparison.

The antioxidant sensor may determine an antioxidant level of the object by analyzing the obtained skin spectrum in 2140.

Figure 22:
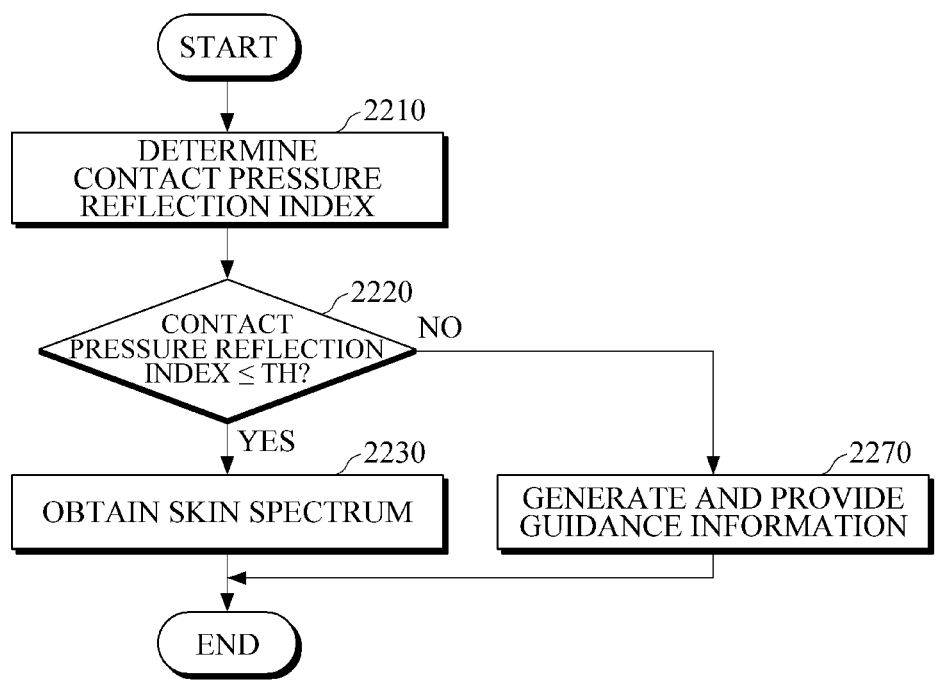
FIG. 22 is a diagram illustrating a method of obtaining a skin spectrum according to an example embodiment.

FIG. 22 is a diagram illustrating an example of a method of obtaining a skin spectrum according to an example embodiment. The skin spectrum obtaining method of FIG. 22 may be an example of the obtaining of a skin spectrum in 2130 of FIG. 21.

Referring to FIG. 22, the antioxidant sensor may determine a contact pressure reflection index by analyzing an image of a contact surface in 2210, and may compare the contact pressure reflection index with a predetermined threshold TH in 2220. Further, in response to the contact pressure reflection index being lower than or equal to a predetermined threshold, the antioxidant sensor may obtain the skin spectrum of the object in 2230.

In addition, the antioxidant sensor may further consider a duration of a status of the contact pressure reflection index in addition to a magnitude thereof. For example, in response to the contact pressure reflection index being lower than or equal to a predetermined threshold and such a state is maintained for a predetermined period of time, the antioxidant sensor may obtain the skin spectrum of the object.

In response to the contact pressure reflection index exceeding a predetermined threshold, the antioxidant sensor may generate information on a low contact pressure and/or guidance information for guiding a user to increase a pressure applied to the object, and may provide the generated information to the user through the output device described above in 2270.

Figure 23:
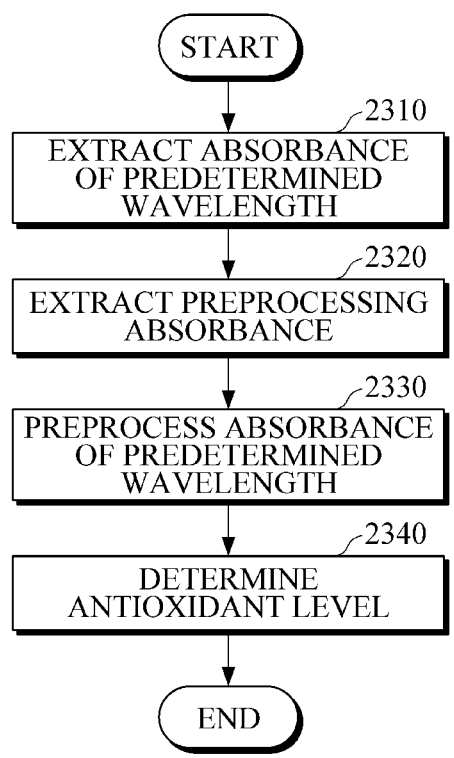
FIG. 23 is a diagram illustrating a method of determining an antioxidant level of an object by analyzing a skin spectrum according to an example embodiment.

FIG. 23 is a diagram illustrating an example of a method of determining an antioxidant level of an object by analyzing a skin spectrum. The antioxidant level determining method of FIG. 23 may be an example of the determining of an antioxidant level in 2140 of FIG. 21.

Referring to FIG. 23, the antioxidant sensor may extract an absorbance of a predetermined wavelength, corresponding to an antioxidant signal, from a skin spectrum in 2310, and may extract an absorbance of another wavelength corresponding to a preprocessing signal, which is used for preprocessing (hereinafter a preprocessing absorbance) in 2320. The predetermined wavelength corresponding to the antioxidant signal may be a blue wavelength; and the another wavelength may be a wavelength different from the predetermined wavelength corresponding to the antioxidant signal, and may be a blue wavelength, a green wavelength, or a red wavelength.

The antioxidant sensor may preprocess the absorbance of the predetermined wavelength based on the preprocessing absorbance in 2330. The antioxidant sensor may normalize the absorbance of the predetermined wavelength corresponding to the antioxidant signal by, for example, subtracting the preprocessing absorbance from the absorbance of the predetermined wavelength or by dividing the absorbance of the predetermined wavelength by the preprocessing absorbance. By normalizing the absorbance of the predetermined wavelength, the antioxidant sensor may eliminate an effect of a substance, other than an antioxidant substance, from the absorbance of the predetermined wavelength corresponding to the antioxidant signal.

The antioxidant sensor may determine an antioxidant level of the object by analyzing the preprocessed absorbance of the predetermined wavelength in 2340.

In response to the antioxidant level being lower than or equal to a predetermined threshold level, the antioxidant sensor may generate information on the antioxidant level and/or information recommending a user to increase the antioxidant level, and may provide the generated information to a user through an output device.

Figure 24:
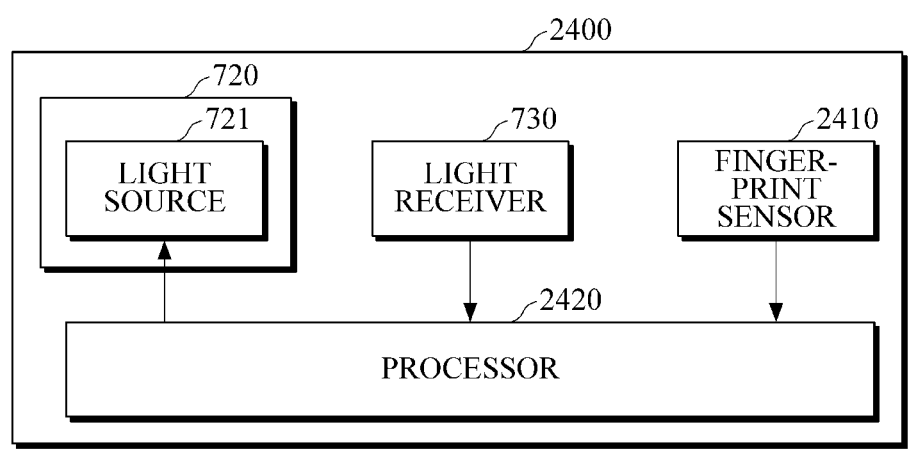
FIG. 24 is a diagram illustrating an antioxidant sensor according to another example embodiment.

FIG. 24 is a diagram illustrating an example of an antioxidant sensor according to another example embodiment. Referring to FIG. 24, the antioxidant sensor 2400 includes a fingerprint sensor 2410, the light source part 720, the light receiver 730, and a processor 2420. Here, the light source part 720 and the light receiver 730 are the same as those described above with reference to FIG. 7, such that detailed description thereof will be omitted.

Once an object touches the fingerprint sensor 2410, the fingerprint sensor 2410 may detect a contact with the object, and may generate an image of a contact surface of the object.

The processor 2420 may recognize a fingerprint by analyzing the image of the contact surface which is generated by the fingerprint sensor 2410, and may recognize a user by comparing the recognized fingerprint with pre-stored fingerprint data.

The processor 2420 may analyze the image of the contact surface which is generated by the fingerprint sensor 2410, and may obtain an antioxidant signal by controlling the light source 721 based on the analysis of the image of the contact surface. For example, the processor 2420 may determine a contact pressure reflection index by analyzing the generated image of the contact surface; and in response to the contact pressure reflection index being lower than or equal to a predetermined threshold, the processor 2420 may drive the light source 721 to obtain an antioxidant signal of the object. Here, the contact pressure reflection index may include at least one of a change in the area of the contact surface, a change in the length of the contact surface, the number of wrinkles in the image of the contact surface, and a degree of the fingerprint being smudged.

In an example embodiment, the processor 2420 may determine a change in the area of the contact surface by analyzing the image of the contact surface. The change in the area may be calculated by, for example, subtracting a preceding value from a current value or by dividing the current value by the preceding value. Further, in response to the change in the area of the contact surface being less than or equal to a first threshold, the processor 2420 may drive the light source 721 to emit light of a predetermined wavelength onto the object, and may obtain an antioxidant signal by controlling the light receiver 730 to receive light returning from the object.

In another example embodiment, the processor 2420 may determine a change in the length of the contact surface by analyzing the image of the contact surface. The length of the contact surface may include a length in any direction such as a length in a long axis direction, a length in a short axis direction, a length in a diagonal direction, and the like; and the change in the length may be calculated by, for example, subtracting a preceding value from a current value or by dividing the current value by the preceding value. In response to the change in the length of the contact surface being less than or equal to a second threshold, the processor 2420 may drive the light source 721 to emit light of a predetermined wavelength onto the object, and may obtain an antioxidant signal by controlling the light receiver 730 to receive light returning from the object.

In yet another example embodiment, the processor 2420 may determine the number of wrinkles in the image of the contact surface by analyzing the image of the contact surface. If the number of wrinkles is less than or equal to a third threshold, the processor 2420 may drive the light source 721 to emit light of a predetermined wavelength onto the object, and may obtain an antioxidant signal by controlling the light receiver 730 to receive light returning from the object.

In still another example embodiment, the processor 2420 may determine a degree of the fingerprint being smudged by analyzing the image of the contact surface. The degree of the fingerprint being smudged may be determined by comparing a current image frame with a preceding image frame. Further, in response to the degree of smudging of the fingerprint being less than a fourth threshold, the processor 2420 may drive the light source 721 to emit light of a predetermined wavelength onto the object, and may obtain an antioxidant signal by controlling the light receiver 730 to receive light returning from the object.

The first threshold, the second threshold, the third threshold, and the fourth threshold may be preset in consideration of pressure at which the antioxidant signal is saturated and stabilized.

In addition, the antioxidant sensor 2400 may further consider a duration of a status of the contact pressure reflection index in addition to a magnitude thereof. For example, in response to the contact pressure reflection index being lower than or equal to a predetermined threshold and such a state is maintained for a predetermined period of time, the processor 2420 may obtain the antioxidant signal.

If the contact pressure reflection index exceeds a predetermined threshold, or even if the contact pressure reflection index is less than or equal to a predetermined threshold, if such a state is not maintained for a predetermined period of time, the processor 2420 may determine that a pressure applied to an object is not sufficient to obtain an antioxidant signal, and may generate information on a low contact pressure and/or information for guiding a user to increase the pressure applied to an object and output the generated information through the output device described above.

Upon obtaining the antioxidant signal, the processor 2420 may determine an antioxidant level of the object by analyzing the obtained antioxidant signal. For example, the processor 2420 may determine the antioxidant level of the object by using an antioxidant level estimation model. Here, the antioxidant level estimation model defines a relationship between an antioxidant signal and an antioxidant level, and may be pre-generated by, for example, regression analysis or machine learning and stored in an internal or an external database of the processor 2420. The antioxidant level estimation model may be built in the form of a mathematical algorithm or a matching table, but is not limited thereto.

In response to an antioxidant level being lower than or equal to a predetermined threshold level, the processor 2420 may generate information on the antioxidant level and/or information recommending a user to increase the antioxidant level and may provide the generated information to a user through the output device described above.

The disclosure can be realized as a computer-readable code written on a computer-readable recording medium. The computer-readable recording medium may be any type of recording device in which data is stored in a computer-readable manner. Examples of the computer-readable recording medium include a ROM, a RAM, a CD-ROM, a magnetic tape, a floppy disc, an optical disk, and the like. Further, the computer-readable recording medium can be distributed over a plurality of computer systems connected to a network so that a computer-readable recording medium is written thereto and executed therefrom in a decentralized manner.

At least one of the components, elements, modules or units described herein may be embodied as various numbers of hardware, software and/or firmware structures that execute respective functions described above, according to an example embodiment. For example, at least one of these components, elements or units may use a direct circuit structure, such as a memory, a processor, a logic circuit, a look-up table, etc. that may execute the respective functions through controls of one or more microprocessors or other control apparatuses. Also, at least one of these components, elements or units may be specifically embodied by a module, a program, or a part of code, which contains one or more executable instructions for performing specified logic functions, and executed by one or more microprocessors or other control apparatuses. Also, at least one of these components, elements or units may further include or implemented by a processor such as a central processing unit (CPU) that performs the respective functions, a microprocessor, or the like. Two or more of these components, elements or units may be combined into one single component, element or unit which performs all operations or functions of the combined two or more components, elements of units. Also, at least part of functions of at least one of these components, elements or units may be performed by another of these components, element or units. Further, although a bus is not illustrated in the block diagrams, communication between the components, elements or units may be performed through the bus. Functional aspects of the above example embodiments may be implemented in algorithms that execute on one or more processors. Furthermore, the components, elements or units represented by a block or processing steps may employ any number of related art techniques for electronics configuration, signal processing and/or control, data processing and the like.

Although a few example embodiments have been shown and described, it would be appreciated by those skilled in the art that changes may be made in example embodiments without departing from the principles and spirit of the disclosure, the scope of which is defined in the claims and their equivalents.

What is claimed is:

1. An antioxidant sensor, comprising:
   a touch sensor configured to detect a contact with an object;
   a first light source configured to emit light of a first wavelength onto the object;
   a light receiver configured to receive light returning from the object; and
   a processor configured to:
   extract an image of a contact surface between the object and the touch sensor by performing contouring based on a sensor value of the touch sensor;
   analyze the extracted image of the contact surface, to obtain a contact pressure reflection index, the contact pressure reflection index comprising a number of wrinkles in the image of the contact surface;
   estimate a pressure applied to the object to be greater than a predetermined pressure threshold based on the number of wrinkles in the image of the contact surface being less than or equal to a predetermined threshold; and drive, based on the estimated pressure being equal to or greater than the predetermined pressure threshold, the first light source to obtain an antioxidant signal of the object.

2. The antioxidant sensor of claim 1, wherein the antioxidant signal comprises a signal associated with carotenoid.

3. The antioxidant sensor of claim 1, wherein the first wavelength comprises a blue wavelength.

4. The antioxidant sensor of claim 1, wherein the contact pressure reflection index further comprises at least one of a change in an area of the contact surface or a change in a length of the contact surface.

5. The antioxidant sensor of claim 1, wherein, based on the number of wrinkles being in a state of being lower than or equal to the predetermined threshold and the state being maintained for a predetermined period of time, the processor is further configured to obtain the antioxidant signal of the object by driving the first light source.

6. The antioxidant sensor of claim 1, wherein, based on a number of wrinkles in another extracted image of the contact surface exceeding the predetermined threshold, the processor is further configured to generate information for guiding a contact pressure between the object and the touch sensor to be increased, and output the information.

7. The antioxidant sensor of claim 1, wherein the light receiver comprises at least one of a photodetector or a spectrometer.

8. The antioxidant sensor of claim 1, further comprising a second light source configured to emit light of a second wavelength onto the object touching the touch sensor,
wherein the processor is further configured to, based on the number of wrinkles being lower than or equal to the predetermined threshold, obtain a preprocessing signal of the object by driving the second light source and preprocess the obtained antioxidant signal based on the obtained preprocessing signal.

9. The antioxidant sensor of claim 8, wherein the second wavelength comprises at least one of a blue wavelength, a green wavelength, or a red wavelength.

10. The antioxidant sensor of claim 8, wherein the processor is further configured to normalize the antioxidant signal by subtracting the preprocessing signal from the antioxidant signal or by dividing the antioxidant signal by the preprocessing signal.

11. The antioxidant sensor of claim 1, wherein the processor is further configured to determine an antioxidant level of the object by analyzing the obtained antioxidant signal.

12. The antioxidant sensor of claim 11, wherein the processor is further configured to determine the antioxidant level of the object by using an antioxidant level estimation model which defines a relationship between the antioxidant signal and the antioxidant level.

13. The antioxidant sensor of claim 11, wherein the processor is further configured to, based on the determined antioxidant level being lower than or equal to a predetermined threshold level, generate information recommending an increase of the antioxidant level and output the information.

14. A method of obtaining an antioxidant signal, the method comprising:
detecting a contact with an object using a touch sensor;
extracting an image of a contact surface between the object and the touch sensor based on a sensor value of the touch sensor;
analyzing the extracted image of the contact surface, to obtain a contact pressure reflection index, the contact pressure reflection index comprising a number of wrinkles in the image of the contact surface;
estimating a pressure applied to the object to be greater than a predetermined pressure threshold based on the number of wrinkles in the image of the contact surface being less than or equal to a predetermined threshold; and
emitting, based on the estimated pressure being equal to or greater than the predetermined pressure threshold, light of a first wavelength onto the object, to obtain an antioxidant signal of the object.

15. The method of claim 14, wherein the antioxidant signal comprises a signal associated with carotenoid.

16. The method of claim 14, wherein the first wavelength comprises a blue wavelength.

17. The method of claim 14, wherein the contact pressure reflection index further comprises at least one of a change in an area of the contact surface or a change in a length of the contact surface.

18. The method of claim 14, wherein the obtaining the antioxidant signal comprises, based on the number of wrinkles being in a state of being lower than or equal to the predetermined threshold and the state being maintained for a predetermined period of time, obtaining the antioxidant signal of the object.

19. The method of claim 14, further comprising:
based on a number of wrinkles in another extracted image of the contact surface exceeding the predetermined threshold, generating information for guiding a contact pressure between the object and the touch sensor to be increased, and outputting the information.

20. The method of claim 14, wherein the obtaining the antioxidant signal comprises:
obtaining a preprocessing signal of the object by emitting light of a second wavelength onto the object; and
preprocessing the obtained antioxidant signal based on the obtained preprocessing signal.

21. The method of claim 20, wherein the second wavelength comprises at least one of a blue wavelength, a green wavelength, or a red wavelength.

22. The method of claim 20, wherein the preprocessing of the obtained antioxidant signal comprises normalizing the antioxidant signal by subtracting the preprocessing signal from the antioxidant signal or by dividing the antioxidant signal by the preprocessing signal.

23. The method of claim 14, further comprising determining an antioxidant level of the object by analyzing the obtained antioxidant signal.

24. The method of claim 23, wherein the determining the antioxidant level comprises determining the antioxidant level of the object by using an antioxidant level estimation model which defines a relationship between the antioxidant signal and the antioxidant level.

25. The method of claim 23, further comprising, based on the determined antioxidant level being lower than or equal to a predetermined threshold level, generating information recommending an increase of the antioxidant level and outputting the information.

* * * * *